United States Patent [19]
Feinberg et al.

[11] Patent Number: 5,965,124
[45] Date of Patent: Oct. 12, 1999

[54] REPLICATION-COMPETENT RECOMBINANT VIRAL VACCINES AND METHOD OF PRODUCING SAME

[75] Inventors: Mark Feinberg, San Francisco, Calif.; Raul Andino, New York; Carolyn Louise Weeks-Levy, Valhalla, both of N.Y.; Patricia Anne Reilly, Glen Rock, N.J.

[73] Assignees: Whitehead Institute for Biomedical Research, Cambridge, Mass.; American Cynamid Company, Parsippany, N.J.

[21] Appl. No.: 08/381,637

[22] Filed: Jan. 31, 1995

Related U.S. Application Data

[63] Continuation of application No. 07/986,729, Dec. 8, 1992, abandoned, which is a continuation-in-part of application No. 07/947,790, Sep. 18, 1992, abandoned, which is a continuation-in-part of application No. 07/804,893, Dec. 6, 1991, abandoned.

[51] Int. Cl.[6] .................................................. A01N 63/00
[52] U.S. Cl. ................... 424/93.21; 435/69.1; 435/69.3; 435/320.1; 435/325; 424/199.1; 424/201.1; 424/217.1; 424/216.1; 514/44; 536/23.1
[58] Field of Search ................................. 435/69.1, 69.3, 435/172.3, 65, 320.1, 325; 424/199.1, 201.1, 217.1, 216.1, 93.21; 514/44; 536/23.1

[56] References Cited

U.S. PATENT DOCUMENTS 5,162,601  11/1992  Slightom .............................. 800/205

FOREIGN PATENT DOCUMENTS

| 0 187 721 | 1/1986 | European Pat. Off. . |
| 3-19691 | 12/1991 | Japan . |
| WO 89/08145 | 9/1989 | WIPO . |
| WO 90/11359 | 10/1990 | WIPO . |
| WO 90/14842 | 12/1990 | WIPO . |
| WO90/15145 | 12/1990 | WIPO . |
| WO 91/18990 | 12/1991 | WIPO . |
| WO 92/03559 | 3/1992 | WIPO . |

OTHER PUBLICATIONS

Fields et al, Virology Third Edition, Lippincott–Raven Press, Chapter 21, Picornaviridae: The viruses and Their Replication, 1996.
Whalen (Emerging Infectious Disease, vol. 2, No. 3:168–175, 1996).
Etlinger, Immunology Today, 13, 2, 52–55, 1992.
Lerner, R.A. et al. (1983) in: The Biology of Immunologic Disease, F.J. Dixon & D.W. Fisher, eds., HP Publishing Co, Inc., New York, NY., pp. 331–338.
Rose, C.S. et al. (1991) Trends in Biotechnol. 9:415–421.
Carrington, J.C. et al. (1988) Proc. Natl. Acad. Sci USA 85:3391–3395.
Blair, W.S. et al. (1990) J. Virol. 64: 1784–1793.
Nicklin, M.J. et al. (1988) J. Virol. 62:4586–4593.
Evans, D.J. et al. (1989) Nature 339: 385–388.
Burke, K. et al. (1989) J. Gen. Virol. 70:2475–2479.
Whelan, S.P.J. and Almond, J.W., Abstract from Europic '91, the Seventh Meeting of the European Study Group on the Molecular Biology of Picornaviruses, The University of Kent at Canterbury, U.K. Aug. 24th–30th, 1991.
Hagino–Yamagishi, K. and Nomoto, A., Abstract from Europic '91, the Seventh Meeting of the European Study Group on the Molecular Biology of Picornaviruses, The University of Kent at Canterbury, U.K. Aug. 24th–30th, 1991.
Almond, J.W. et al., Abstract F6 in Abstracts from Europic '91, the Seventh Meeting of the European Study Group on the Molecular Biology of Picornaviruses, The University of Kent at Canterbury, U.K. Aug. 24th–30th, 1991.
Konig, Herbert, et al., "Purification and Partial Characterization of Poliovirus Protease 2A by Means of a Functional Assay," *J. of Virology,* pp. 1243–1250 (1988).
Pallai, Peter V., et al., "Cleavage of Synthetic Peptides by purified Polioviruses 3C Proteinase," *J. Biol Chemistry* 264:9738–9741 (1989).
Ansardi, David C., et al., "Coinfection with Recombinant Vaccinia Viruses Expressing Poliovirus P1 and P3 Proteins Results in Polyprotein Processing and Formation of Empty Capsid Structures," *J. of Virology* 65:2088–2092 (1991).
Deideu, J.F. et al., Abstract D30 in abstracts from Europic '91, the Seventh Meeting of the European Study Group on the Molecular Biology of Picornaviruses, The University of Kent at Canterbury, U.K. 24th–30th 1991.
Murdin, A.D. et al., Abstract from Europic '91, the Seventh Meeting of the European Study Group on the Molecular Biology of Picornaviruses, The University of Kent at Canterbury, U.K. 24th–30th 1991.
Evans, D.J. et al., Abstract D12 from Europic '91, the Seventh Meeting of the European Study Group on the Molecular Biology of Picornaviruses, The University of Kent at Canterbury, U.K. 24th–30th 1991.
Burke, K.L. et al., "Antigen Chimaeras of Poliovirus as Potential New Vaccines," *Nature* 332:81–82 (1988).

(List continued on next page.)

*Primary Examiner*—Bruce R. Campell
*Assistant Examiner*—Dave Trong Nguyen
*Attorney, Agent, or Firm*—Hamilton, Brook, Smith & Reynolds, P.C.

[57] ABSTRACT

Replication-competent recombinant viruses, particularly replication-competent recombinant polioviruses, which include (1) exogenous nucleic acid sequences which encode an exogenous polypeptide and (2) a nucleic acid sequence which encodes an artificial proteolytic cleavage site for a viral or cellular protease which proteolytically processes (cleaves) the precursor protein produced by the parent virus and uses therefor. The recombinant precursor is cleaved into the usual array of constituent proteins, freeing the exogenous polypeptide. Replication-competent recombinant viruses are useful as vaccines against bacterial, viral, fungal and yeast infections, parasitic diseases, cancer and allergies.

41 Claims, 9 Drawing Sheets

OTHER PUBLICATIONS

Iizuka, N. et al., "Construction of Less Neurovirulent Polioviruses by Introducing Deletions into the 5' Noncoding Sequence of the Genome," *Journal of Virology* 63(12):5354–5363 (1989).

Kuge, S. and Nomoto, A., "Construction of Viable Deletion and Insertion Mutants of the Sabin Strain of Type 1 Poliovirus: Function of the 5' Noncoding Sequence in Viral Replication," *Journal of Virology* 61(5):1478–1487 (1987).

Kohara, M. et al., "A Recombinant Virus between the Sabin 1 and Sabin 3 Vaccine Strains of Poliovirus as a Possible Candidate for a New Type 3 Poliovirus Live Vaccine Strain," *Journal of Virology* 62(8):2828–2835 (1988).

Feinberg, M. et al., "Novel Recombinant Poliovirus Vectors" Abst., The Rockefeller Univ., NY, NY 10021, USA. The Gladstone Institute of Virology & Immunology. University of California, San Francisco, CA 94110, for the Third International Symposium on Positive Strand RNA Viruses in Clearwater, FL, Sep. 19–24, 1992.

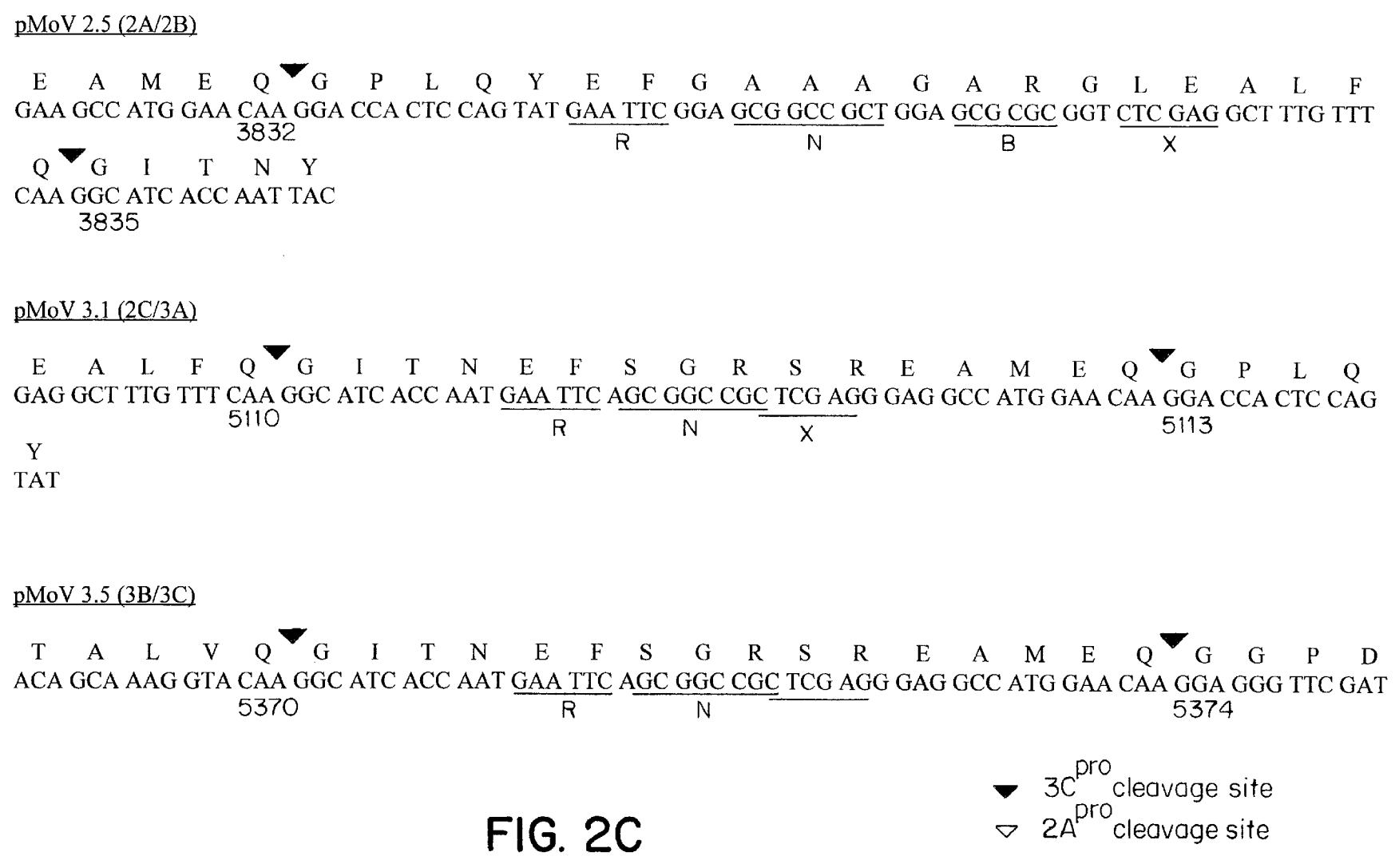

pMoV 2.5 (2A/2B)

E   A   M   E   Q ▶ G   P   L   Q   Y   E   F   G   A   A   A   G   A   R   G   L   E   A   L   F
GAA GCC ATG GAA CAA GGA CCA CTC CAG TAT GAA TTC GGA GCG GCC GCT GGA GCG GCC CGC GGT (*) = unfractionated sample

REPLICATION-COMPETENT RECOMBINANT VIRAL VACCINES AND METHOD OF PRODUCING SAME

RELATED APPLICATIONS

This application is a continuation of application Ser. No. 07/986,729 filed Dec. 8, 1992, abandoned, which is a Continuation-in-Part of Ser. No. 07/947,790, filed Sep. 18, 1992, abandoned, which is a Continuation-in-Part of Ser. No. 07/804,893, filed Dec. 6, 1991, abandoned.

BACKGROUND

Presently, there are many types of vaccines used to immunize individuals against disease. Although those available are generally safe and, at least to some extent, effective in inducing an immune response, all have limitations. In addition, for some diseases, there is no effective vaccine. The development of alternatives to presently-available vaccines and of new vaccines to protect against diseases for which no vaccine is currently available would be an important step in reducing the morbidity and mortality caused by many diseases.

SUMMARY OF THE INVENTION

The present invention relates to replication-competent recombinant viruses which include exogenous nucleic acid sequences which encode an exogenous polypeptide or protein which is expressed as a component of a recombinant polyprotein precursor which is subsequently proteolytically processed by viral and/or cellular enzymes. As a result, the encoded exogenous polypeptide is released. The replication-competent viruses can be animal (non-human) viruses (e.g., vertebrate or mammalian viruses), human viruses, or plant viruses. It further relates to replication-competent recombinant viruses, particularly polioviruses, in which the recombinant genome includes an exogenous nucleic acid sequence (or sequences) encoding an exogenous polypeptide or polypeptides to be expressed and one or more nucleic acid sequences encoding the corresponding number of artificial proteolytic cleavage sites and which express the encoded polypeptide(s) and induce production of antibodies specific for the polypeptide(s) in a mammal into which they are introduced. Appropriately selected replication-competent viruses are useful to deliver the exogenous protein to an individual, such as a vertebrate, particularly mammals and even more particularly, humans into whom they are introduced. In the case of a plant virus, for example, a replication-competent plant virus can be inserted into seeds or the plant at another stage in its development in such a manner that the encoded exogenous polypeptide is expressed and processed. Such an exogenous polypeptide can be used, for example, to protect the plant against disease or attack by insects. The plants can be used to deliver the vaccine by oral consumption.

The replication-competent recombinant viruses of the present invention include a wide variety of types of viruses, such as picornaviruses (e.g., enteroviruses, poliovirus, foot and mouth disease virus (FMDV), rhinovirus, echoviruses, Hepatitis A virus), Togaviruses (e.g., Sindbis virus and rubella virus), and Flaviviruses (e.g., yellow fever virus). The type of virus used is determined in part by the target exogenous antigen(s) to be expressed, the route by which the resulting recombinant viruses are to be administered, and the character of the immune response desired.

In particular, the present invention relates to replication-competent recombinant polioviruses which differ from the parent poliovirus in that they have been modified in such a manner that they are not pathogenic and contain exogenous nucleic acid sequences and one or more artificial proteolytic cleavage sites, such that during the course of the viral infection, they stably express the encoded exogenous product as a component of a recombinant polyprotein precursor. The precursor is proteolytically cleaved, releasing the normal poliovirus proteins and the encoded exogenous protein. In addition, the replication-competent recombinant viruses may contain a polylinker sequence (EcoR1, Not1, BssH2, and Xho1) to facilitate ease of insertion of the desired foreign nucleic acid sequences. They can also include a poly-amino acid tract, such as a poly-glycine tract, which is generally adjacent to the inserted sequence so as to enhance the structural flexibility of the region and potentially increase the efficiency of proteolytic processing.

The present invention also relates to a novel method of producing recombinant viruses, in which exogenous nucleic acid sequences are inserted into the viral genome. In the method of the present invention, basic aspects of the viral life cycle are utilized, with the result that the recombinant virus produces its normal protein components and replicates and the amino acid sequence encoded by the exogenous nucleic acid sequence(s) (the exogenous protein) is produced in significant quantity in infected cells. In the present method, a parent virus whose genome encodes a polyprotein precursor which is proteolytically processed by viral or cellular enzymes to produce one or more mature proteins is modified as follows: An exogenous nucleic acid sequence which encodes a polypeptide to be produced and a nucleic acid sequence or sequences which encode(s) an artificial proteolytic cleavage site or sites for a viral or a cellular protease which proteolytically processes (cleaves) the precursor polyprotein produced during the viral life cycle by the parent virus are introduced into the viral genome, producing a recombinant virus. The sequences can be introduced into the virus genome at any location, provided that their presence does not disrupt a viral sequence necessary for viral replication. For example, the two sequences can be inserted at any native site at which the polyprotein is processed to produce two native proteins (i.e., at any site at which the native polyprotein is normally proteolytically cleaved). In those instances in which the exogenous nucleic acid sequences are inserted at an end of a viral sequence encoding a protein, only one proteolytic processing sequence is needed. If more than one exogenous nucleic acid sequence encoding a polypeptide to be produced is introduced into the viral genome, additional proteolytic cleavage site-encoding nucleic acid sequences may be needed. For example, if two or more polypeptide-encoding nucleic acid sequences are introduced within the viral genome (internally) and it is desired that the encoded proteins be cleaved to produce two or more separate proteins, then a sufficient number of nucleic acid sequences encoding cleavage sites must also be introduced. For example, if two exogenous nucleic acid sequences, each encoding a protein to be produced, are introduced within a viral genome and two separate (individual) proteins are desired, three or four nucleic acid sequences encoding proteolytic cleavage sites are needed (i.e., three if the two proteins are encoded by two nucleic acid sequences present in the viral genome without intervening nucleic acid sequences and four if the two nucleic acid sequences are separated by an intervening nucleic acid sequence, the encoded product of which must be removed to "separate" the two encoded proteins). In those instances in which the sequences are inserted within (not at an end of) a virus genome, two proteolytic processing sequences are needed to allow both ends of the exogenous nucleic acid sequence to be freed; these sequences can be the same or different.

In one embodiment of the present invention, two sequences are introduced into a parent virus genome between the first or unique start codon and the second codon at the 5' end of a viral sequence encoding a viral protein in such a manner that the order in the recombinant genome is: 5' untranslated region of the parent virus—unique start codon of the parent virus—exogenous nucleic acid sequence encoding a product to be expressed—nucleic acid sequence encoding an artificial proteolytic cleavage site—second codon of the parent virus—remainder of the parent nucleic acid sequence. In another embodiment in which an exogenous nucleic acid sequence encoding an exogenous polypeptide is incorporated within the viral genome, the order of sequences in the resulting recombinant viral genome is: 5' untranslated region of the parent virus— unique start codon of the parent virus—the initial codon(s) of the translated region of the parent virus—nucleic acid sequence encoding an artificial proteolytic cleavage site— exogenous nucleic acid sequence—nucleic acid sequence encoding an artificial proteolytic cleavage site—remainder of the parent virus genome. The encoded proteolytic cleavage sites can be the same or different.

In one embodiment of the present invention, in which recombinant poliovirus (which expresses an exogenous nucleic acid sequence or sequences) is produced, a nucleic acid sequence encoding a protein (e.g., an antigen) to be expressed and a nucleic acid sequence(s) encoding an artificial recognition sequence or sequences for the poliovirus 3C protease are introduced into the genome of a parent poliovirus. In another embodiment, a nucleic acid sequence or sequences encoding an artificial recognition sequence(s) for the poliovirus 2A protease is introduced into the viral genome along with one or more nucleic acid sequences encoding a protein(s) to be expressed. In the case of DNA viruses, the genome will be manipulated in its DNA form. In the case of RNA viruses, the genome is manipulated in its cDNA form. Both of these are referred to as the genome of the parent virus. In the embodiment in which an exogenous nucleic acid sequence encoding an exogenous polypeptide is incorporated into the end of the poliovirus genome, the resulting recombinant poliovirus genome structure is as follows: 5' untranslated region of the parent poliovirus—poliovirus unique start codon—exogenous nucleic acid sequence—artificial poliovirus 3C or 2A protease recognition site—second codon of the poliovirus genome—remainder of the poliovirus genome. In the embodiment in which an exogenous nucleic acid sequence encoding an exogenous polypeptide is incorporated at a site within the parent poliovirus genome (i.e., an internal site), the resulting recombinant poliovirus genome is as follows: 5' untranslated region of the parent poliovirus—poliovirus unique start codon—polio protein encoding regions(s)—nucleic acid sequence encoding artificial 3C protease recognition site or the 2A protease recognition site—exogenous nucleic acid sequence(s)—nucleic acid sequence encoding artificial 3C protease recognition site or 2A protease recognition site—remainder of the poliovirus. In those cases in which more than one protein or polypeptide is to be expressed, more than one exogenous nucleic acid sequence is included in the recombinant replication-competent poliovirus (i.e., a nucleic acid sequence encoding each of the proteins or polypeptides to be expressed), together with the appropriate number of artificial proteolytic cleavage sites, as described above.

When the modified polioviral genome is translated, a larger than normal precursor is made, but is cleaved appropriately into the usual array of constituent poliovirus proteins by the 3C and/or 2A protease(s) present in the parent poliovirus. The 3c and/or 2A protease(s) also accurately recognize(s) and cleave(s) the artificial recognition (proteolytic cleavage) site, freeing the exogenous polypeptide encoded by the exogenous nucleic acid sequences. As described herein, the recombinant polioviruses of the present invention express the encoded exogenous protein(s) in detectable amounts. The parental virus continues to replicate and the native proteins are produced as well.

The replication-competent recombinant viruses of the present invention, as exemplified by the recombinant poliovirus, can be used as vaccines against bacterial, viral, fungal (e.g., yeast) infections, parasitic diseases, cancer or allergies. They can also be used to deliver a contraceptive (e.g., a sperm antigen). Vaccines and contraceptive compositions which are or include replication-competent recombination viruses as described herein are also the subject of the present invention.

Recombinant polioviruses vaccines of the present invention are particularly advantageous when induction of mucosal immunity is required to prevent infection. For example, effective induction of mucosal immunity would be advantageous in preventing or lessening infection by HIV, rotavirus, respiratory syncytial virus (RSV), Hepatitis A virus, poliovirus, papilloma virus, measles virus and the influenza viruses. The recombinant viruses are also useful for inducing immunity against bacterial diseases, such as those caused by *Vibrio cholerae* and enterotoxigenic *E. coli*. In addition, the recombinant poliovirus can be used to provide protection against infection by more than one organism by introducing more than one exogenous nucleic acid sequence (i.e., two or more nucleic acid sequences, each of which encodes a different antigen) into the genome of the parent poliovirus. Alternatively, a mixture or cocktail of two or more recombinant polioviruses, each of which expresses a different antigen, can be used to immunize an individual against more than one organism or infectious agent. Through utilization of the emerging tools of molecular biology to develop improved or novel vaccines, the derivation of "the ideal vaccine" described by the Task Force on Child Survival as one in which "single administration at birth will provide protection from multiple diseases" may hopefully be realized.

The recombinant viruses can also be used to produce the exogenous polypeptide in tissue culture, which can be isolated or separated from the cells and virus in which it is produced. They can be used to produce the exogenous polypeptide in vertebrate cells, mammalian cells, including human cells, and plant cells.

BRIEF DESCRIPTION OF THE DRAWINGS

FIG. 1 is a schematic representation of a recominant poliovirus of the present invention, in which the poliovirus genome modifications which permit insertion of exogenous nucleic acid sequences at an end of the polioviral genome and expression of exogenous polypeptides are shown. The recombinant poliovirus shows the beginning sequence of the poliovirus genome which includes the unique start codon (SEQ ID NO: 24 and 25) and the exogenous nucleic acid sequence which is followed by an artificial proteolytic site and the remaining sequence of the poliovirus genome (SEQ ID NO: 26 and 27). Also shown is the pattern of proteolytic processing of the viral 3C protease, as it cleaves both the native poliovirus polyprotein (PO) precursor and the exogenous protein insert.

FIG. 2 is a schematic representation of recombinant polioviruses of the present invention, in which insertion of exogenous nucleic acid sequences at an end and within the polioviral genome which results in expression of exogenous polypeptides are shown. Also shown is a polyglycine tract, adjacent to the inserted sequence, which enhances structural flexibility of the region. The recombinant polioviruses are as follows: pMOV 1.3 (SEQ ID NO: 28 and 29, pMOV 2.1 (SEQ ID NO: 30 and 31), pMOV 2.2 (SEQ ID NO: 32 and 33), pMOV 2.5 (SEQ ID NO: 34 and 35), pMOV 3.1 (SEQ ID NO: 36 and 37) and pMOV 3.5 (SEQ ID NO: 38 and 39).

FIG. 3 is a photograph of results of a plaque assay, which shows the phenotype of parent poliovirus and recombinant poliovirus. In the plaque assay shown, HeLa cells were infected with parent poliovirus (A) or recombinant polioviruses carrying: antigenic epitopes derived from the rotavirus VP4 protein (B, C and D), or the entire coding sequence from the mature cholera toxin subunit B (CTB)(E).

FIG. 4 presents results of assays which show the expression and processing of a recombinant polioviruses carrying the Vibrio cholerae B toxin subunit or rotavirus VP4 sequences.

FIG. 4A is a photograph of a Western blot prepared using extracts from HeLa cells infected with either parent poliovirus (lane 1) or the cholera toxin B-poliovirus recombinant virus described in Example 2 (lane 2). Results show that the B subunit is expressed and appropriately processed within the context of the recombinant poliovirus (indicated by arrow).

FIG. 4B is a photograph of extracts from the same HeLa cells infected with either a parent poliovirus (lane 1) or the cholera toxin B(CTB)-polio recombinant virus (lane 5) (Example 2) and probed with rabbit antibodies recognizing poliovirus structural proteins. Results show that a larger than normal P1 polyprotein precursor is made in the poliovirus recombinant, but appropriate proteolytic processing ensues, generating the normal complement of poliovirus protein products, as well as release of exogenous CTB protein generated from the CTB nucleotide sequences. Lanes 2–4 contain recombinant polioviruses carrying antigenic epitopes (21 to 104 amino acids in length) derived from the rotavirus VP4 protein.

FIG. 5 shows results of SDS-PAGE analysis carried out to analyze the structure and composition of the recombinant virions. The pattern of migration of the two viruses (parent and recombinant) is virtually indistinguishable, suggesting that the viral particles of the recombinant viruses have a normal structure and protein composition. The identity of the poliovirus capsid proteins is indicated.

FIG. 6 shows results of Western blot analysis carried out to determine the ability of the recombinant polioviruses to induce an immune response in a vaccinated host, compared to control values and mock injections.

DETAILED DESCRIPTION OF THE INVENTION

Figure 1A:
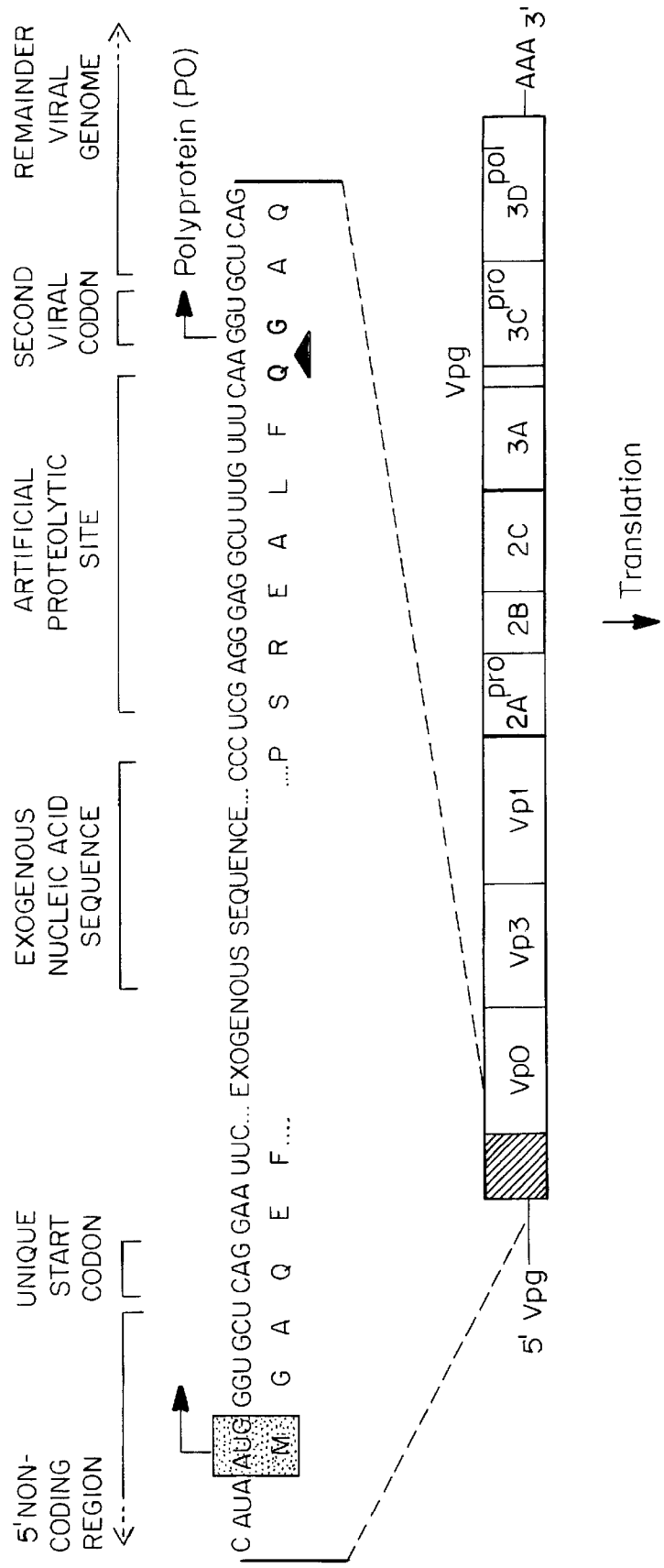

The present invention relates to recombinant replication-competent viruses which include an exogenous nucleic acid sequence which encodes an exogenous polyprotein to be produced during the viral life cycle and a nucleic acid sequence which encodes an artificial proteolytic cleavage site for a viral or cellular protease which cleaves the precursor polyprotein produced by the parent virus. The two types of sequences can be present at any location in the parent virus genome, as long as their presence does not disrupt a viral sequence necessary for viral replication.

The present invention is based on Applicants' demonstration that an exogenous nucleic acid sequence encoding an exogenous polypeptide can be incorporated into the genome of a virus at an end of the viral genome or at a site within the viral genome (i.e., at an internal site) and be produced during the viral life cycle as a precursor polyprotein which is cleaved by viral or cellular proteases which cleave the precursor polyprotein normally produced by the parent virus (i.e., the virus into which the exogenous nucleic acid sequence was introduced). In one embodiment in which an exogenous nucleic acid sequence encoding an exogenous polypeptide is incorporated into the end of the viral genome, the order of sequences in the resulting recombinant viral genome is: 5' untranslated region of the parent virus—unique start codon of the parent virus—exogenous nucleic acid sequence—nucleic acid sequence encoding an artificial proteolytic cleavage site—second codon of the parent virus—remainder of the parent virus genome. The portion of the recombinant genome which is the 5' untranslated region of the viral genome can be all or a portion of the 5' untranslated region as it occurs in the parent virus. In another embodiment in which an exogenous nucleic acid sequence encoding an exogenous polypeptide is incorporated within the viral genome, the order of sequences in the resulting recombinant viral genome is: 5' untranslated region of the parent virus—unique start codon(s) of the parent virus—the initial codon(s) of the translated region of the parent virus—nucleic acid sequence encoding an artificial proteolytic cleavage site—exogenous nucleic acid sequence—nucleic acid sequence encoding an artificial proteolytic cleavage site—remainder of the parent virus genome.

The encoded exogenous polypeptide is expressed in the context of normal viral protein translation as a component of a recombinant or fusion precursor polypeptide (which includes the exogenous polypeptide, an artificial proteolytic recognition site or sites and the viral polyprotein). The recombinant precursor polypeptide is proteolytically processed by viral or cellular protease(s) which process the parent viral precursor polyprotein, resulting in release of the free exogenous protein from the viral proteins. The virus modified to include the exogenous sequences is referred to as the parent virus, which can be a native virus (either pathogenic or, preferably, non-pathogenic), an attenuated virus, a vaccine strain or a recombinant virus. As used herein, the term polypeptide includes proteins or portions thereof (peptides), fusions of two or more proteins or peptides and fusions of a protein and a peptide.

In a particular embodiment, Applicants have produced replication-competent recombinant poliovirus which includes an exogenous nucleic acid sequence encoding an exogenous protein to be expressed and a nucleic acid sequence encoding an artificial proteolytic cleavage site for the poliovirus 3C protease and/or 2A protease, incorporated into the end of the poliovirus genome or at a site within the poliovirus genome. They have demonstrated that the exogenous protein is expressed and freed from the poliovirus proteins by proteolytic processing. The resulting replication-competent recombinant polioviruses differ from the parent virus in that they include exogenous nucleic acid sequence (s) encoding an exogenous polypeptide or polypeptides and one or more artificial proteolytic cleavage sites and express the exogenous product during viral infection. The parent poliovirus can be a native or wild-type poliovirus, attenuated poliovirus, a vaccine strain or a recombinant or genetically engineered poliovirus (in which case the altered or mutated sequence does not encode an exogenous protein useful for the purposes described herein for the polioviruses which are the present invention).

In one embodiment of the present invention, the exogenous nucleic acid sequence encoding the exogenous polypeptide and the nucleic acid sequence encoding the artificial proteolytic cleavage sites are positioned at an end of the polioviral genome, between the unique start codon and the second codon of the poliovirus genome such that the order of sequences in the recombinant genome is as follows: 5' untranslated region of the poliovirus genome—poliovirus unique start (first) codon—exogenous nucleic acid sequence—artificial protease recognition site—second codon of the poliovirus genome—remainder of the poliovirus genome. As a result, expression of the recombinant polioviral genome produces a recombinant or fusion polyprotein precursor which includes the exogenous protein, the artificial protease cleavage site and the poliovirus polyprotein. Applicants have shown that proteolytic processing of the recombinant polyprotein precursor by the protease for which the artificial cleavage site is included results in production of the normal poliovirus protein components and freeing of the exogenous protein. Viral replication also ensues, but the exogenous protein is not included in the poliovirus virion.

Figure 1B:
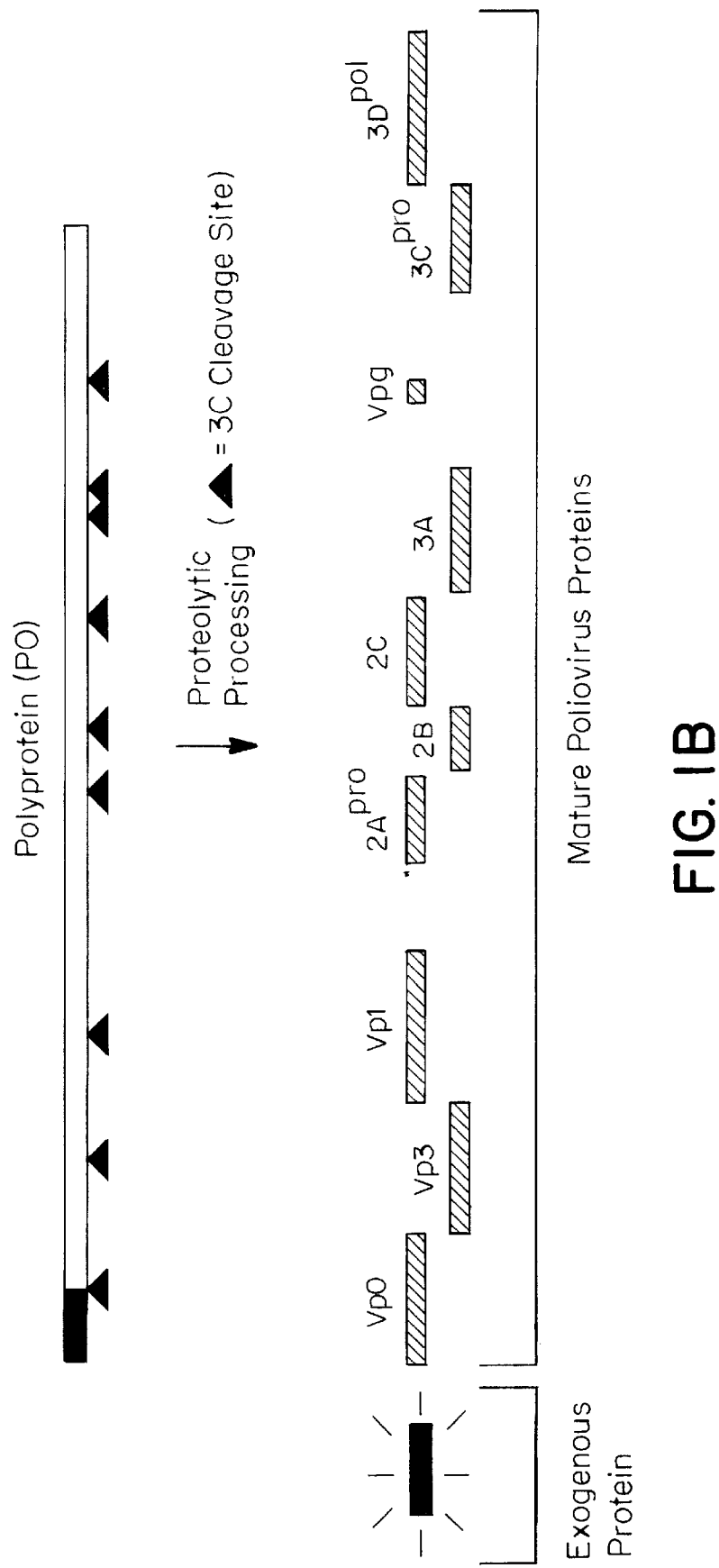
Figure 2A:
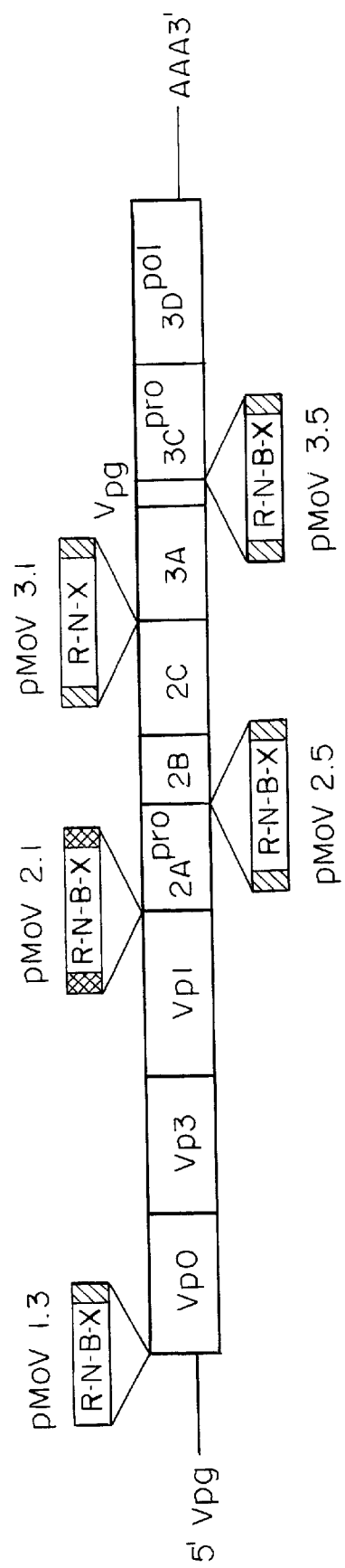
Figure 2B:
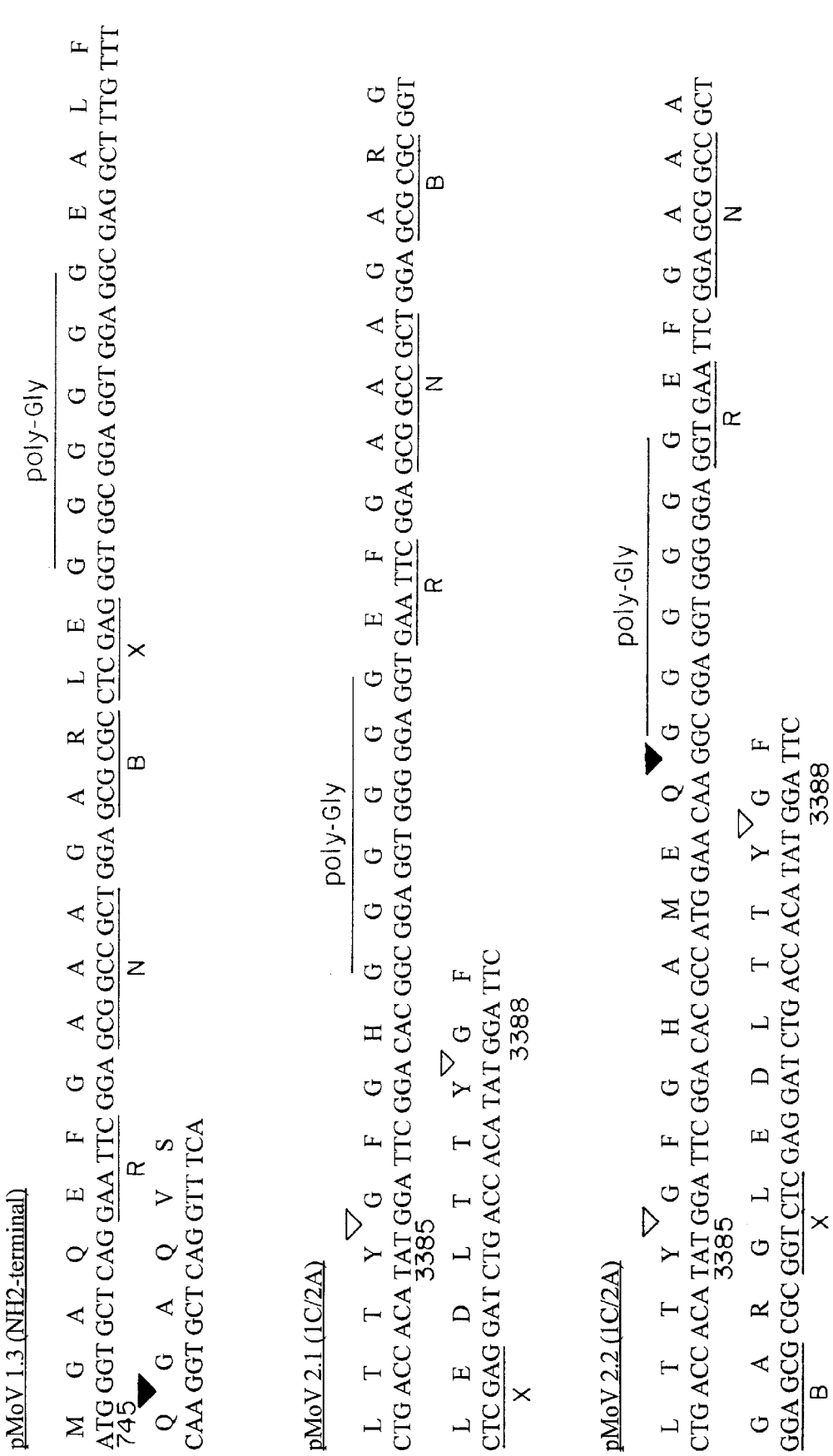

Two recombinant polioviruses of the present invention, in which the exogenous nucleic acid and the nucleic acid sequence encoding an artificial proteolytic cleavage site are incorporated at an end of the poliovirus genome, are represented in FIG. 1 and FIG. 2 (pMOV 1.3). The recombinant poliovirus genome includes nucleic acid sequences (immediately 3' of the unique start codon) which encode the five amino acid residues present at the amino terminus of the Mahoney type 1 strain of poliovirus. The presence of these sequences is not necessary, but their presence may affect efficiency of expression. As represented in FIG. 2, the recombinant poliovirus genome can also include a polyglycine tract adjacent to the inserted (exogenous) sequences.

Exogenous nucleic acid sequences encoding a protein or polypeptide to be expressed can be introduced within the viral genome, as exemplified by the poliovirus genome. As shown in FIG. 2, there are a number of additional locations within the poliovirus genome at which the exogenous nucleic acid sequence encoding the exogenous polypeptide and the nucleic acid sequences encoding the artificial proteolytic cleavage sites can be positioned to produce replication-competent recombinant polioviruses that express the encoded product. These sites within the genome of the poliovirus include the junction between the Vp1 coding region and the 2A coding region, the junction between the 2A coding region and the 2B coding region and the junction between the 2C coding region and the 3A coding region. Polylinker/proteolytic processing motifs have been inserted at these sites and the resulting recombinant polioviruses have been shown to be replication-competent. Using the methods described herein and known methods, an exogenous nucleic acid sequence or sequences can be introduced at these sites. Insertion of a polylinker/proteolytic motif at the junction of the Vpg encoding region and the 3C encoding region abrogated viral replication.

To facilitate processing of exogenous sequences within the interior of the viral polyprotein, it is necessary to include the appropriate proteolytic processing signals at both ends of the insert. Therefore, the order of sequences in the polioviral genome in which the exogenous nucleic acid sequence encoding the exogenous polypeptide and the nucleic acid sequence encoding the artificial proteolytic cleavage sites are, for example, inserted at the junction between the Vp1 coding region and the 2A coding region, is as follows: 5' untranslated region of the poliovirus genome—poliovirus unique start codon—Vp0 coding region—Vp3 coding region—Vp1 coding region—nucleic acid sequence encoding artificial 3C protease recognition site or 2A protease recognition site—exogenous nucleic acid sequence—nucleic acid sequence encoding artificial 3C protease recognition site or 2A protease recognition site—remainder of the poliovirus genome.

The determination that there are multiple sites in the poliovirus genome at which insertion of exogenous nucleic acid sequences can be made to produce replication-competent recombinant polioviruses means, in a broader sense, that there is considerable flexibility and variation possible in designing and producing recombinant viruses useful, for example, as vaccines and protein production. One or more exogenous nucleic acid sequences encoding an exogenous protein or polypeptide to be expressed and proteolytically processed can be introduced at one or more of the sites in (at an end or within) the viral genome described herein. In addition, other sites at which insertions can be made without abrogating replicative ability of the virus can be identified. It is possible that some exogenous nucleic acid sequences will be better tolerated or more efficiently expressed and/or proteolytically processed if they are incorporated at a particular site in the viral genome. Whether this is correct or not can be assessed using the methods described herein and recombinant viruses produced accordingly, as exemplified with polioviruses.

Additional features may be incorporated into the design of replication-competent recombinant viruses, such as polylinker sequences (e.g., EcoR1, Not1, BssH2, and Xho1) to facilitate the ease of insertion of desired foreign sequences into the recombinant vector. Also, variants, such as a poly-glycine tract, may be inserted adjacent to the inserted sequence so as to enhance the structural flexibility of the region and potentially increase the efficiency of proteolytic processing.

More than one nucleic acid sequence encoding an exogenous protein or polypeptide to be produced can be included in the recombinant replication-competent virus which, as a result, produces the corresponding number of protein or polypeptides. The two or more nucleic acid sequences can each encode a different product or can encode the same product (e.g., if enhanced production of a protein or polypeptide is desired). Further, for poliovirus, the proteolytic cleavage site(s) can be the 3C cleavage site, the 2A cleavage site or both.

Although the present invention is exemplified by production of recombinant poliovirus, any virus in which proteolytic processing of a viral precursor protein occurs can be modified to produce recombinant virus which expresses an exogenous protein and processes it appropriately. For example, recombinant picornaviruses(e.g., enteroviruses, poliovirus, FMDV, rhinovirus, echoviruses, Hepatitis A virus) and recombinant Flaviviruses (e.g., yellow fever virus) can be produced and used in a similar manner to that described for recombinant poliovirus.

The present method of producing replication-competent recombinant virus which expresses and proteolytically processes an exogenous protein is as follows: A virus which in its natural life cycle (referred to as parent virus) produces a protein precursor which is proteolytically processed by viral or cellular protease(s) is modified, using known genetic engineering techniques (Sambrook, J. et al., *Molecular Cloning: A Laboratory Manual* (2d ed.), Cold Spring Harbor Laboratory Press (1989), to introduce at least two types of nucleic acid sequences into the viral genome: an exogenous nucleic acid sequence (a nucleic acid sequence obtained from a source other than the type of virus into which it is introduced) encoding an exogenous protein or polypeptide to be expressed and processed by the recombinant virus and a nucleic acid sequence encoding an artificial recognition site for the viral and/or cellular protease(s) which will process the expressed recombinant protein to release viral and exogenous proteins. An additional type of nucleic acid sequence, such as a poly-glycine tract, may be inserted adjacent to the exogenous nucleic acid sequence to enhance structural flexibility of the region and potentially increase the efficiency.

Construction of a poliovirus vector cDNA clone, illustrative of this invention, is described in Example 1. One or more "units", which each include an exogenous nucleic acid sequence or sequences encoding an exogenous product(s), one or more artificial proteolytic recognition site(s) and, optionally, additional nucleic acid sequences such as the poly-glycine tract, can be introduced in this manner. For example, one "unit" which includes a nucleic acid sequence encoding an exogenous protein antigen against which an immune response is desired and an artificial recognition site for proteolytic processing can be introduced at the 5' end of the viral genome. Alternatively, two or more such "units" or one "unit" which includes nucleic acid sequences encoding more than one protein or polypeptide and the appropriate number of proteolytic cleavage sites (e.g., to result in expression and release of two or more different protein antigens or two copies of one protein antigen) can be introduced into the viral genome. The nucleic acid sequences encoding proteins or polypeptides to be expressed can be in the "unit" in tandem (i.e., with no intervening sequences) or separated by nucleic acids which do not encode the protein or polypeptide to be expressed. One or more units can be introduced into some or all of the sites in the viral genome. The resulting recombinant polyprotein precursor will include one or more exogenous proteins or peptides and one or more proteolytic cleavage sites. Processing of the recombinant polyprotein precursor results in freeing of the exogenous product or products.

Figures 3A, 3B, 3C, 3D, 3E:
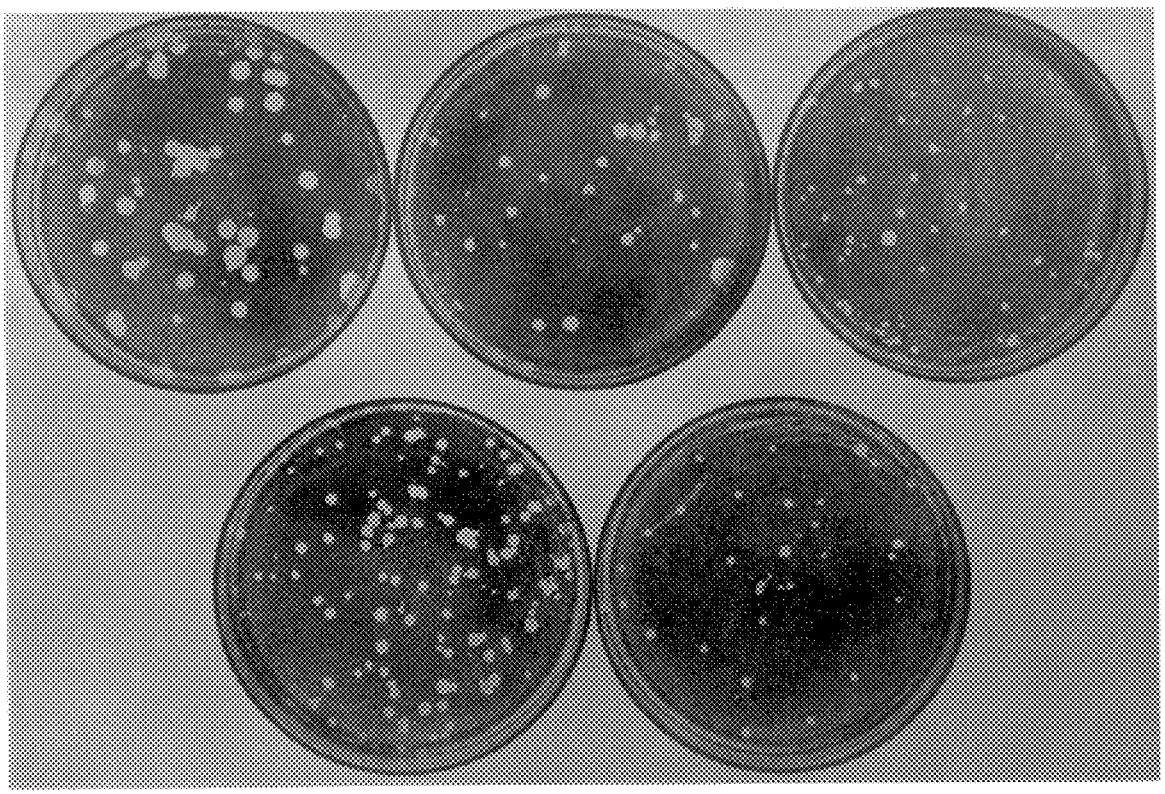
Figure 4A:
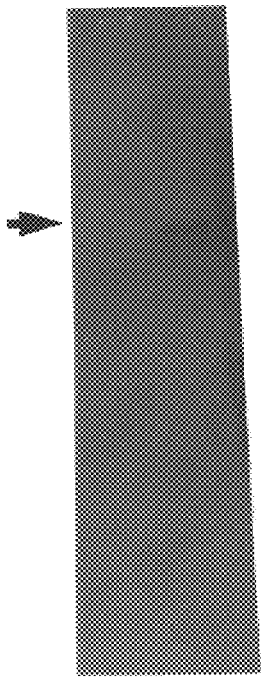
Figure 4B:
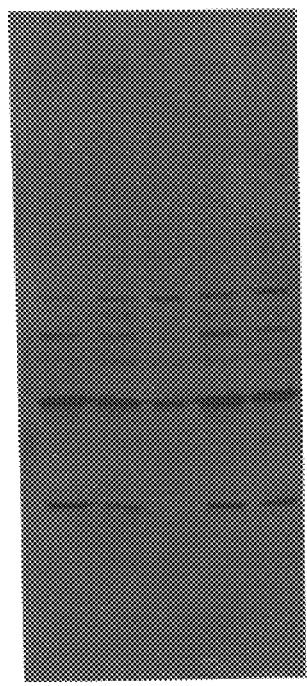
Figure 5:
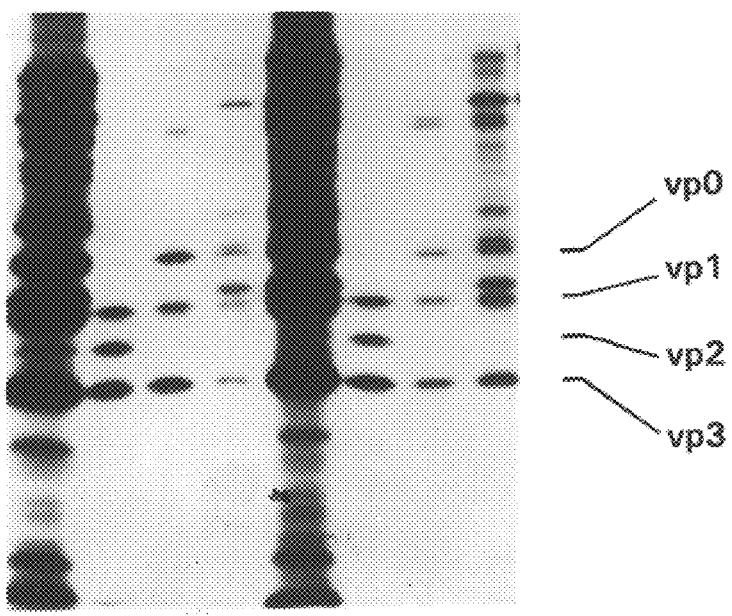

Recombinant virus, such as recombinant poliovirus described herein, can be used to induce an immune response against an antigen in an individual and, thus, provide protection against challenge or infection by the exogenous pathogen (bacterial, viral, fungal, parasitic) in which the antigen occurs. They are, therefore, useful as vaccines to provide protection against such pathogens. As described in Example 2, a recombinant poliovirus has been constructed which includes nucleic acid sequences encoding antigenic epitopes from the rotavirus VP4 protein. As also described in Example 2, a recombinant poliovirus has been constructed which includes the entire coding region from the cholera toxin subunit B. Recombinant polioviruses which include nucleic acid sequences encoding influenza A virus antigens or the toxin coregulated pilus (tcpA) of Vibrio cholerae have also been produced. The phenotype of these recombinants and of parent poliovirus is shown in FIG. 3. The recombinant poliovirus containing the entire coding region from the cholera toxin subunit B was expressed in HeLa cells and its expression and processing assessed. Results showed that the B subunit is expressed and appropriately processed within the context of the recombinant virus (FIG. 4A). Results also showed that a larger than normal P1 polyprotein is made in the recombinant poliovirus, but that appropriate proteolytic processing occurred, generating the normal complement of poliovirus protein products and free cholera toxin B subunit sequences (FIG. 4B). Recombinant poliovirus containing antigenic epitopes (21–104 amino acids in length) derived from the rotavirus VP4 protein was also expressed in HeLa cells. Lanes 2–4 of FIG. 4B contain recombinant polioviruses carrying these epitopes.

Example 3 describes assessment of the immunogenicity of recombinant polioviruses produced as described herein. Transgenic mice that express the human poliovirus receptor were infected by intramuscular injection with recombinant polioviruses that express the entire cholera toxin B subunit (CTB) within the context of Mahoney or Sabin-based vectors. Control mice were either mock-infected or infected with a recombinant virus that expresses the *Vibrio cholerae* pilin. Western blot analysis showed (FIG. 6) that the mice immunized with the Mahoney-based CTB-recombinant poliovirus clearly contained IgG antibodies reactive with the CTB monomer and pentamer. The control mice, as expected, lacked such specific antibodies. In addition, mice immunized with the Sabin-based CTB-recombinant poliovirus did not produce, in this one case, CTB-specific antibody reactivity. The reason for this is not clear but may relate to the replicative characteristics of the recombinant polioviruses and may be resolvable by increasing the dose of recombinant virus vaccine.

Recombinant poliovirus containing nucleic acid sequences encoding other antigens against which an immune response is desired can be produced in a manner similar to that described for the cholera toxin subunit B and the rotavirus VP4 protein. The recombinant polioviruses are particularly useful in preventing diseases (or lessening the severity to which they occur) that may require induction of mucosal immunity to prevent infection. For example, the recombinant polioviruses may be particularly useful in providing protection against or lessen the severity of infection by the HIV, rotavirus, RSV, hepatitis A virus and the influenza viruses.

The mucosal surfaces of the human body cover more than 400 m2 and represent the largest area of contact between the immune system and the environment. The total number of lymphoid cells associated with mucosal surfaces exceeds those of all other lymphoid tissues combined, and these cells are responsible for the synthesis of at least 60% of the total immunoglobulin produced daily (Childers, N. K et al., *Annu. Rev. Microbiol.* 43:503–536 (1989)). The presence of specific IgA antibodies in secretions such as tears, saliva and milk in the absence of local antigen exposure has given rise to the concept of a common mucosal immune system. The progeny of immune cells sensitized in the gut-associated lymphoreticular tissues (GALT) are believed to migrate to, and protect, distant mucosal surfaces. In spite of the extent and importance of the mucosal immune system, there is relatively little known about the determinants of cellular and humoral immunity on mucosal surfaces. Experimental evaluation of these issues has been limited by the relative inaccessibility of responding lymphocytes, as well as the difficulty of delivering well characterized antigens to reproducible target sites. Recombinant polioviruses should permit the delivery of well characterized antigens in a reproducible fashion, and may ameliorate some of these experimental barriers. A number of viral and bacterial diseases of significant importance cannot be prevented by vaccination at present. These include diarrheal disease caused by rotaviruses, respiratory diseases resulting from RSV infection, and bacterial gastroenteritis induced by *V. cholerae* or enterotoxogenic *E. coli*. Mucosal immunity is generated following natural infection by these pathogens, which confers significant or complete resistance to reinfection. The recombinant poliovirus of the subject invention can be used to deliver the relevant protective antigens to the mucosal immune system and, thus, provide a new vaccine strategy.

Poliovirus vaccines have been used extensively and are very safe and effective. The biologically active molecular clones of poliovirus utilized include the poliovirus type 1 (Mahoney strain) (Racaniello, V. et al., *Proc. Natl. Acad Sci., U.S.A.* 78:4887–4891 (1981)) and the Sabin vaccine strains of poliovirus types 1, 2 and 3 (Omata, T. et al., *Gene* 32:1–10 (1984); Toyoda, H. et al., *J. Mol. Bio.* 174:561–585 (1984)). Derivatives of the polioviruses can also be made which are less likely to revert to a virulent form or can be made avirulent from the virulent form through site directed mutagenesis through the insertion, deletion, and/or modification of nucleotide sequences.

Recombinant poliovirus vaccines may be useful replacements for presently used oral poliovirus vaccine, which requires a mixture of three different attenuated strains (PV1, PV2 and PV3), each of which has variable levels of antigenic potency and a slight risk of reversion to the wild-type pathogenic form. PV1 is considered both the safest and most antigenic component, while PV3 is known to suffer from the highest frequency of reversion to a pathogenic type. Enteroviruses: Polioviruses, Coxsackieviruses, Echoviruses, and Newer Enteroviruses Melnick, J. L. In: *Virology* (2d ed.), D. N. Fields, D. M. Knipe et al. (ed.) Raven Press Ltd, N.Y. 1990, pp. 549–604; Nkowane, B. M. et al., Vaccine-Associated Paralytic Poliomyelitis United States: 1973–1984 *JAMA*, 257:1335–1340 (1987); Melnick, J. L. Population Genetics Applied to Live Poliovirus Vaccine, *Am. J. Pub. Health* 52:472–483 (1962). A recombinant poliovirus based on PV1, into which PV2 and PV3 components are inserted, may prove to be a safer vaccine than those presently available. In addition, with recombinant polioviruses based on PV1, it may be possible to achieve effective immunity against all poliovirus strains by provision of a maximally attenuated, antigenically potent recombinant virus carrying antigenic determinants from all three poliovirus serotypes.

Particular advantages to the use of the recombinant poliovirus as a vaccine are that it is genetically stable and reproducibly carries the inserted information as the oliovirus genome spreads from cell to cell as it replicates. As a result, immunization should be effective with a limited number of doses of the recombinant poliovirus. In addition, because the introduced antigens are expressed within infected cells, both cell-mediated and humoral immunity should be stimulated. Although the exogenous nucleic acid sequences are carried by the recombinant polioviruses and expressed during the replicative cycle, the exogenous proteins are not included in the mature virus particle. Thus, the virion structure and host range of the recombinant poliovirus are not altered by the exogenous proteins. A number of important variables limit the efficacy of available vaccines, especially as they are utilized in developing countries. While some of these issues are of a practical or economic nature, others have a biological basis. Immunization with measles vaccine is a good example of a biological barrier, which the present invention is useful to overcome. Measles is responsible for the death of 2 million children annually in the developing world. Bloom, B. R., *Nature*, 342:115–120 (1989). While an effective vaccine exists to prevent measles virus infection, the presence of maternally derived antibodies that neutralize the vaccine severely comprises its efficacy in young children. Murphy, B. R. and R. M. Chanock, In: *Virology* (2d ed.), B. N. Fields et al. (ed.), Raven Press, N.Y., pp. 469–502 (1990); Preblud, S. R. and S. L. Katz, *Vaccines*, S. A. Plotkin and E. A. Mortimer, W. B. Saunders Publishing, Philadelphia (1988). In developing nations, the epidemiology of measles infection is such that many children contract the disease before they can be effectively vaccinated. Recombinant polioviruses carrying antigens derived from the measles virus may help overcome such barriers. Poliovirus vaccines are given shortly after birth, and their efficacy is not significantly impaired by the presence of maternally derived antibodies. A polio-measles recombinant virus would express measles antigens in infected cells, permitting the generation of an immune response. However, because the measles antigens are not included in the recombinant virus particle, the replication of the vaccine vector should not be compromised.

There are additional areas in which vaccines of the present invention should be useful. For example, diarrheal diseases are estimated to cause between 5–10 million deaths each year. Institute of Medicine, New Vaccine Development: Establishing Priorities, National Academy Press, Washington, D. D. (1985). Rotaviruses are the single most important etiologic agents of severe diarrhea in infants and young children, and are believed to cause approximately a million deaths in this population each year. Kapikian, A. Z. and R. M. Chanock, In: *Virology* (3d ed.), B. N. Field et al. (Ed.), Raven Press, N.Y., pp. 1353–1404 (1990). While significant progress has been made in defining the host immune response to rotavirus infection, vaccine efforts have been limited by the genetic complexity of the virus and the limited efficacy of available attenuated vaccine strains. Similarly, antigens of *V. cholerae* have been described that are the likely targets of a protective immune response. However, candidate vaccines against cholera have been limited either by undesirable side effects or inadequate immunogenicity. Recombinant polioviruses carrying immunogenic, but non-pathogenic, protective determinants from rotavirus and *V. cholerae* warrant evaluation as candidate vaccines.

Respiratory diseases caused by infectious agents result in an estimated 10 million deaths each year, with RSV representing the primary viral pathogen. McIntosh, K. and R. M. Chanock, In: *Virology*, (2d ed.), B. N. Field et al. (Ed.), Raven Press, N.Y., pp. 1045–1074 (1990). Efforts to develop a RSV vaccine have been unsuccessful to date, but significant progress has been made in identifying protective antigens. For an RSV vaccine to be effective, it must induce mucosal immunity, and be delivered soon after birth, yet avoid the neutralizing effects of maternally-derived antibodies. Recombinant RSV-polioviruses could potentially fulfill all of these criteria.

Prevention of disease caused by hepatitis B virus is also a target for vaccines prepared in accordance with the present invention.

Hepatitis B virus belongs to the family of viruses called the Hepadnaviridae. The virus contains a small circular fragment of DNA that is partially single-stranded. The infectious virion also contains a DNA polymerase that makes the DNA genome fully double-stranded. The replicative cycle of hepatitis B virus (HBV) involves formation of an RNA intermediate.

Hepatitis B virus is distributed globally around the world. Humans appear to be the principal reservoir for the virus, even though the surface antigen of the virus has been found in some non-human primate species. It is estimated that in the United States, there are 22 cases of hepatitis per 100,000 population, an estimate which is thought to be underestimated by as much as 10-fold. Of those cases, 45% are attributed to hepatitis B. Thus, there are an estimated 1–1.25 million persons with chronic hepatitis B infections in the United States.

The most efficient route of transmission of the hepatitis B virus is parenteral introduction. Virus has been found in other bodily secretions of those infected, but other modes of transmission of the virus have not been well-established.

HBV has also been implicated in the development of primary hepatocellular carcinoma in those chronically infected with the virus. This disease is most prevalent in Africa, China, Southeast Asia, Alaska and the coast of Greenland. Hepatocellular carcinoma frequency follows the same general geographic pattern of distribution as that of persistent HBV infection.

Prevention of disease caused by *Bordetella pertussis* is a further target for the present invention. This bacterium is the causative agent of pertussis or whooping cough, a serious and potentially fatal infectious disease of the respiratory tract. Pertussis vaccines currently used contain chemically inactivated whole cells of *B. Pertussis*. Acellular pertussis vaccines have been developed which are based on material obtained by chemical and physical fractionation of *B. pertussis* cultures.

In addition, vaccines have been described which are prepared by purifying individual specific pertussis antigens, which are then combined to form the vaccine (published European Patent Application 484,621). One of the antigens included in such a vaccine is the 69 kilodalton (69 kD) outer membrane protein (Shahin, R. D. et al., *Abstracts of the 89th Annual Meeting of the American Society for Microbiology*, page 51 (1989)). This antigen may be produced in accordance with the present invention.

Prevention and therapy of disease caused by Herpes viruses (Herpetoviridae) is still another target for the present invention. Herpes viruses are large DNA viruses which establish latent infections which may persist for the life of the host. After a period of quiescence, the virus may be reactivated by such stimuli as immunosuppression or irradiation.

Herpes simplex virus type 1 is the causative agent for oral lesions such as "cold sores". Herpes simplex virus type 2 is the causative agent for genital herpes, which has further been implicated in carcinoma of the cervix. These Herpes viruses are widespread in the population and, at present, there is no registered vaccine against these viruses.

Vaccines under development against Herpes viruses utilize glycoproteins, which are the viral proteins essential for the entry of the virus into cells. Of particular interest are the glycoproteins designated gD of Herpes simplex types 1 and 2. The DNA sequences of the genes encoding gD-1 and gD-2 are set forth in U. S. Pat. No. 4,818,694 and 4,891,315. Either of the glycoproteins may be produced in accordance with the present invention. Also of interest are the glycoproteins designated gB of Herpes simplex types 1 and 2. The DNA sequences of the genes encoding gB-1 and gB-2 are set forth in Stuve, L. L. et al., *J. Virology*, 61:326–335 (1987) and Bzik, D. J. et al., *Virology*, 155:322–333 (1986). Either of these glycoproteins may be produced in accordance with the present invention.

Disease caused by rotavirus is a further target for the present invention. Rotavirus is now recognized by the WHO as a major cause of infantile gastroenteritis and a high priority has been placed on control of this disease by the production of a suitable vaccine (*Bull. W.H.O.*, 61:251–254 (1983)).

The rotavirus genome consists of eleven segments of double-stranded RNA. These genes encode the production of at least six structural proteins of the virus, which occur in a double-shelled arrangement in complete virus particles. Three of these proteins are outer shell glycoproteins.

An approach being pursued in the development of such a vaccine is to produce by recombinant DNA technology several of these outer shell glycoproteins of rotaviruses. One of these glycoproteins is designated VP7. The DNA sequence of the gene encoding VP7 is set forth in Both, G. W., et al., *Proc. Natl. Acad. Sci. U.S.A.*, 80:3091–3095 (1983). This glycoprotein may be produced in accordance with the present invention.

Any DNA sequence which encodes a peptide or protein of an exogenous organism, which, when expressed, produces protective immunity against such organism or against a condition or disorder caused by an antigen, can be considered exogenous nucleic acids for the purpose of the present invention. Nucleic acid sequences encoding one or more exogenous polypeptides (e.g., antigens or epitopes) can be included in a vaccine of the present invention. If more than one exogenous antigen or epitope is encoded by the exogenous nucleic acid sequences, they can be antigens or epitopes of a single pathogen or antigens or epitopes from more than one (different) pathogens. In a preferred embodiment, such an organism is a pathogenic microorganism. For example, such an exogenous epitope may be found on bacteria, parasites, viruses or fungi which are the causative agents of diseases or disorders. In addition, epitopes of allergens, sperm and cancer cells can be used. Such bacteria, parasites, viruses or fungi include but are not limited to, those listed below.

The replication-competent recombinant viruses are useful as vaccines against a wide variety of pathogens. For example, DNA or RNA can be obtained from any of the organisms listed below and used to produce the recombinant viruses.

PARASITES:
Plasmodium spp.
Eimeria spp.
Schistosoma spp.
Trypanosoma spp.
Babesin spp.
Leishmania spp.
CryPtosporidia spp.
Toxoplasma spp.
Pneumocystis spp.
BACTERIA:
*Vibrio cholerae*
*Streptococcus pyogenes*
*Neisseria menigitidis*
*Neisseria gonorrhosae*
*Corynabacteria diphtheriae*
*Clostridium tetani*
*Branhamella catarrhalis*
*Bordetella pertussis*
Haemonhilus spp. (e.g., influenzae)
Chlamydia spp.
Enterotoxigenic *Escherichia coli*
VIRUSES:
Human Immunodeficiency virus, type I
Human Immunodeficiency virus, type II
Simian Immunodeficiency virus
Human T lymphotropic virus, type I and II
Respiratory syncytial virus
Hepatitis A virus
Hepatitis B virus Hepatitis C virus
Non-A, Non-B Hepatitis virus
Herpes simplex virus, type I
Herpes simplex virus, type II
Cytomegalovirus
Influenza virus
Parainfluenza virus
Poliovirus
Rotavirus
Coronavirus
Rubella virus
Measles virus
Mumps virus
Varicella
Epstein Barr virus
Adenovirus
Papilloma virus
Yellow Fever virus
Rabies virus
FUNGI:
Candida spp. (especially albicans)
Cryptococcus spp. (especially neoformans)
Blastomyces spp. (dermatitidis)
Histoplasma spp. (especially capsulatum)
Coccidioides spp. (especially immitis)
Paracoccidioides spp. (especially brasiliensis)
Aspergillus spp.

Potentially useful antigens for vaccine formulations can be identified by various criteria, such as the antigen's involvement in neutralization of a pathogen's infectivity (Norrby, E., 1985, Summary, In: *Vaccines* 85, Larnet, R. A., R. M. Chanock, and F. Brown (eds)., Cold Spring Harbor Laboratory, Cold Spring Harbor, N.Y., pp. 388–389), type or group specificity, recognition by patients' antisera or immune cells, and/or the demonstration of protective effects of antisera or immune cells specific for the antigen. In addition, the encoded epitope(s) should preferably display a small or no degree of antigenic variation in time or amongst different isolates of the same pathogen.

Peptides or proteins which are known to contain antigenic determinants can be incorporated into recombinant viruses. If specific antigens are unknown, identification and characterization of immunoreactive sequences should be carried out. One way in which to accomplish this is through the use of monoclonal antibodies generated to the surface or other molecules of a pathogen. The peptide sequences capable of being recognized by the antibodies are defined epitopes. Alternatively, small synthetic peptides conjugated to carrier molecules can be tested for generation of monoclonal antibodies that bind to the sites corresponding to the peptide, on the intact molecule (see, e.g., Wilson et al., *Cell* 37:767 (1984)). Other methods known in the art which may be employed for the identification and characterization of antigenic determinants are also within the scope of the invention.

The exogenous proteins in the vaccine formulations of the invention can also comprise an epitope of an exogenous organism. When the exogenous polypeptide is expressed in a vertebrate host, it elicits an immune response that protects against a condition or disorder caused by an antigen containing the epitope. For example, in this embodiment of the invention, exogenous proteins which encode an epitope(s) or protein(s) of snake venom, bee venom, a hormone, sperm (for contraception), an allergy-inducing antigen or any other antigen to which an immune response is desired, may be used. In another embodiment, a tumor-specific antigen can be expressed as a recombinant exogenous protein, for induction of a protective immune response against cancer.

The gene sequences encoding the exogenous protein to be expressed by the recombinant virus according to the present invention, can be isolated by techniques known in the art, including but not limited to, purification from genomic DNA of the microorganism, by cDNA synthesis from RNA of the microorganism, by recombinant DNA methods (Maniatis et al., *Molecular Cloning, A Laboratory Manual*, 1982, Cold Spring Harbor Laboratory, Cold Spring Harbor, N.Y.), or by chemical synthesis.

When they are used as vaccines, the recombinant viruses of the present invention are administered to an individual using known methods. They will generally be administered by the same routes by which conventional (presently-available) vaccines are administered and/or by routes which mimic the route by which infection by the pathogen of interest occurs. For example, recombinant poliovirus vaccines can be administered orally and others, such as recombinant measles or recombinant Flavivirus vaccines, can be administered subcutaneously. They can be administered in a vaccine composition which includes, in addition to the replication-competent recombinant virus, a physiologically acceptable carrier. The composition may also include an immunostimulating agent or adjuvant, flavoring agent, or stabilizer.

Recombinant viruses of the present invention, particularly recombinant polioviruses, can also be used as a system for producing the exogenous polyprotein in host cells, such as mammalian, particularly human, cells or other cell types (e.g., mammalian cells modified to have a poliovirus receptor). The exogenous protein is then isolated methods.

In either application (i.e., immunization or tissue culture production) the exogenous nucleic acid sequence introduced into the virus can be one obtained from a source in which it occurs naturally, produced using genetic engineering methods or synthesized chemically. The exogenous nucleic acid sequence introduced into the virus can encode an entire antigen against which an immune response is desired or antigenic epitopes or portions. The size of the nucleic acid sequence which can be inserted into the viral genome appears to be unlimited. The maximal size of the exogenous nucleic acid sequences can be determined, such as by assessing its effect on viral replication, as described herein. Exogenous nucleic acid sequences encoding at least 150 additional amino acids (i.e., 450 nucleotides) have been inserted into the poliovirus genome without significant compromise of viral replication efficiency. Inserted sequences are expected to present to the host immune system, antigenic structures defined both by primary sequence and structural conformation.

A plant virus can also be used as the parent virus, into which exogenous nucleic acid sequences are introduced, as described herein. For example, a plant virus with a DNA genome (e.g., cauliflower mosaic virus) or a plant virus with an RNA genome (e.g., tobacco mosaic virus, turnip yellow mosaic virus) can be used. They can be modified, by introducing an exogenous nucleic acid sequence (or sequences) which encode an exogenous polypeptide (e.g, a toxin against an insect or disease) to be expressed in a plant. The resulting replication-competent recombinant plant virus is then introduced into plants (e.g., into seeds or at another stage in plant development), in which the exogenous polypeptide is produced. For example, an exogenous nucleic acid sequence encoding a toxin, such as a scorpion or spider toxin, can be introduced in such a manner that they are expressed in plants, which are protected against insects which feed upon them. In addition, plants in which the exogenous nucleic acid sequence is expressed can be administered orally as a source of the encoded protein or polypeptide.

Similarly, the parent virus can be an animal virus, which is modified to include an exogenous nucleic acid sequence to be expressed in an animal (e.g., to protect or immunize the animal against a pathogen or to provide a growth enhancing factor).

The subject invention will now be illustrated by the following examples, which are not intended to be limiting in any way.

EXAMPLES

Example 1
Construction of Poliovirus Vector cDNA Clone

All manipulations of molecular clones followed standard recombinant DNA methodologies (Ausubel, F. M. et al. *Current Protocols In Molecular Biology*, Greene Publishing-Wiley Interscience, New York, 1987). The biologically active molecular clones of poliovirus utilized include the poliovirus type 1 (Mahoney strain) (Racaniello, V. et al., *Proc. Natl. Acad Sci., U.S.A*. 78:4887–4891 (1981)) and the Sabin vaccine strains of poliovirus types 1, 2 and 3 (Omata, T. et al., *Gene* 32:1–10 (1984); Toyoda, H. et al., *J. Mol. Bio*. 174:561–585 (1984)). These molecular clones have been modified by the insertion of a T7 RNA polymerase promoter at the 5' end of the viral genome to facilitate in vitro transcription by T7 RNA polymerase of infectious poliovirus RNA. Ausubel, F. M. et al., *Current Protocols in Molecular Biology*, Greene Publishing-Wiley Interscience, N.Y. (1987). The poliovirus genomes have been further modified to include an in-frame synthetic polylinker containing a variety of restriction enzyme recognition sites (i.e., EcoRI and XhoI). The sequences inserted within the poliovirus genome include at their 3' border these sequences encoding the recognition and cleavage sites for the poliovirus 3C protease (AXXQG) (Palmenberg, A. C., *Ann. Rev. Microbio*. 44:603–623(1990)). These modifications were performed by a version of the polymerase chain reaction (PCR) known as overlap extension. (Horton, R. M. et al., *Biotechniques* 8:528–535 (1990)). It is illustrated as follows using the example of type 1 poliovirus.

In brief, two independent PCR reactions were performed using oligonucleotides 1 and 2, and 3 and 4 (see the Table) to amplify portions of the poliovirus genome from positions 1 to 740, and 740 to 1540, respectively.

TABLE 1

PRIMERS FOR AMPLIFICATION

| Oligonucleotide Number | Sequence | |
|---|---|---|
| 1- | 5'-TAC GGT CGA CCT AAT TAC GAC TCA CTA TAG G-3' | (SEQ ID #1) |
| 2- | 5'-TTG AAA CAA AGC CTC CCT CGA GGG GAA TTC CTG AGC ACC CAT TAT G-3' | (SEQ ID #2) |
| 3- | 5'-CCC TCG AGG GAG GCT TTG TTT CAA GGT GCT CAG GTT TCA-3' | (SEQ ID #3) |
| 4- | 5'-ATT ATC TGG TGC GGG AAC ACA AAG GC-3' | (SEQ ID #4) |
| 5- | 5'-TCA GGA ATT CAC ACC TCA AAA TAT T-3' | (SEQ ID #5) |
| 6- | 5'-TCA GCT CGA GGG ATT TGC CAT ACT AAT-3' | (SEQ ID #6) |

PCR products containing the fragment to be inserted were purified by agarose gel electrophoresis, and a second PCR amplification was performed with oligonucleotide primers 1 and 4. The 1582 base pair (bp) DNA fragment resulting from this amplification represents the 42 nucleotide insert (carrying the novel restriction enzyme sites and sequences encoding proteolytic processing signals) and sequences 1 to 740, and 740 to 1540. (The 42 nucleotide insert was inserted between bases 740 and 741.) This fragment was digested with SaI 1 and Aat2, purified by gel electrophoresis and ligated to SaI 1-Aat2 digested poliovirus clone pSR-XpA (a previously described plasmid containing a full length poliovirus cDNA clone (Andino, R. et al., *Cell* 63:369–380 (1990)). The resulting plasmid (referred to as pMV2.2) was linearized by digestion with ClaI and the in vitro synthesis of viral RNA by T7 polymerase was performed by the conventional protocol (Ausubel, F. M. et al., *Current Protocols In Molecular Biology*, Greene Publishing-Wiley Interscience, New York, 1987).

Replication-competent poliovirus was recovered by transfection of in vitro synthesized poliovirus RNA into HeLa S3 cells, as described (Luthman, H. et al., *Nucl. Acids Res*. 11:1295–1308 (1983)). The recovered virus was characterized by standard techniques with respect to replicative capacity, structural composition and nucleotide sequence (Ausubel, F. M. et al., *Current Protocols In Molecular Biology*, Greene Publishing-Wiley Interscience, New York, 1987).

Exogenous genetic sequences derived from a variety of viral and bacterial pathogens have been expressed in these recombinant polioviruses. The general strategy utilized is illustrated by the example of the complete cholera toxin B subunit, as follows. Oligonucleotides having the following sequences (chosen to permit in-frame insertion into the poliovirus vector) were used to amplify the entire cholera toxin B subunit coding region contained in the plasmid pJM17 (Pearson, D. N. et al., *Proc. Natl. Acad. Sci., U.S.A*. 79:2978–2980 (1982)):

5'-TCA GGA ATT CAC ACC TCA AAA TAT T-3' (SEQ ID #5)

5'-TCA GCT CGA GGG ATT TGC CAT ACT AAT-3' (SEQ ID #6).

These are primers 5 and 6 presented in Table 1.

The resulting 312 bp DNA was digested with EcoRI and XhoI (sites introduced via the PCR primers) and ligated to EcoRI and XhoI-cleaved pMV2.2. The resulting plasmid was designated as pPCH-52 and the virus obtained following RNA transfection as PCH-52. Similar approaches were used to insert sequences derived from plasmid clones of the toxin-coregulated pilus of *Vibrio cholerae* (tcpA) (Sun, D. et al., *Infect. Immun*. 59:114–118 (1991)), the rotavirus VP4 gene (Gorziglla, M. et al., *Proc. Natl. Acad. Sci., U.S.A*. 87:7155–7159 (1990)) and the influenza A virus hemagglutinin gene (Wiley, D. C. et al., *Ann. Rev. Biochem*.

56:365–394 (1987)). For tcpA, the nucleic acid sequence inserted corresponded to the carboxy terminal of amino acids (157–199) of the protein. For influenza A, the nucleic acid sequence inserted corresponded to amino acids 134–284.

Immunologic characterization of the recombinant polioviruses to document appropriate expression and processing of the poliovirus constituents, as well as the inserted sequences, was performed by Western blot analysis (Ausubel, F. M. et al., *Current Protocols In Molecular Biology*, Greene Publishing-Wiley Interscience, New York, 1987). Preservation of the native virion composition and structure was verified by conventional sucrose gradient (15–30%) centrifugation of metabolically-labelled (35S) lysates of infected cells. Gradient fractions were then analyzed by standard SDS-PAGE analysis (Ausubel, F. M. et al., *Current Protocols In Molecular Biology*, Greene Publishing-Wiley Interscience, New York, 1987).

Example 2
Construction and Assessment of a Recombinant Poliovirus Carrying the Vibrio Cholerae B Toxin Subunit Recombinant polioviruses were constructed containing either the entire coding region from the cholera toxin subunit B (103 amino acids) or several portions of Rotavirus VP4 capsid protein (21–104 amino acids in length). DNA fragments encoding Subunit B or VP4 peptides were amplified and their ends modified by including the appropriate restriction sites for cloning purposes. Expressed in isolation from the toxin A subunit, cholera B subunit is not toxic but can provide an antigenic stimulus to raise a protective immune response. DNA fragments were inserted in the poliovirus vector cDNA clone and RNA was transcribed from the resulting plasmid. The cholera toxin subunit B and rotavirus VP4 recombinant cDNA clones were separately transfected into HeLa cells. Recombinant poliovirus plaques were obtained after incubation at 37° C. for 3 days (FIG. 2). FIG. 2 shows the morphology of the parent and recombinant poliovirus plaque. Extracts prepared from HeLa cells infected with either wild-type poliovirus (lane 1) or the cholera toxin B-poliovirus recombinant virus (lane 2) were electrophoresed on SDS PAGE gels and analyzed by Western blot (FIG. 3A). The Western blot was developed with rabbit antisera specific for the intact cholera toxin (A and B subunits). As can be seen, the B subunit is expressed and appropriately processed within the context of the recombinant poliovirus (indicated by arrow).

Extracts from the same HeLa cells infected with either a parent poliovirus (FIG. 3B, lane 1), or the cholera toxin B-polio recombinant virus (FIG. 3B, lane 5) were probed with rabbit antibodies recognizing poliovirus structural proteins. As can be seen, a larger than normal P1 polyprotein is made in the poliovirus recombinants, due to the presence of the exogenous polypeptide. Appropriate proteolytic processing ensues generating the normal complement of poliovirus protein products, as well as release of the exogenous cholera toxin sequences. Immunologic characterization of recombinant viruses was performed by Western blot analysis (Ausubel, F. M. et al., *Current Protocols in Molecular Biology*, Greene Publishing-Wiley Interscience, New York, 1987). Preservation of native virion structure is confirmed with analysis by conventional density gradient centrifugation and Western blot analysis (Ausubel, F. M. et al., *Current Protocols in Molecular Biology*, Greene Publishing-Wiley Interscience, New York, 1987).

Example 3
Assessment of the Immunogenicity of Recombinant Polioviruses

The experimental model for the initial immunogenicity studies employed transgenic mice that express the human poliovirus receptor (Ren et al., *Cell* 63:353–362 (1990), kindly provided by Dr. Vincent Racaniello). Transgenic mice were infected by intramuscular injection with recombinant polioviruses (50 µl of a $2\times10^8$ pfu/ml stock) that express the entire cholera toxin B subunit (CTB) within the context of Mahoney or Sabin-based vectors (MOSB and MsSB, respectively). Control mice were either mock infected or infected with a recombinant virus that expresses the Vibrio cholerae pilin (TcpA)(MoPi). Mice were infected on two occasions separated by a period of 30 days. After 43 days, vaccinated mice received an intraperitoneal injection of 10 µg of purified CTB (Calbiochem) in incomplete Freund's adjuvant. Five days later, mice were bled and their sera were tested for the presence of IgG antibodies reactive with purified CTB. Antibodies reactive with CTB were detected by Western blot analysis, as follows. CTB (5 ng) was subjected to SDS-PAGE separation in a single wide lane of a 10% polyacrylamide gel, and transferred to nitrocellulose. Sera (diluted 1:100) from immunized animals were loaded into independent lanes of a multi-slot apparatus (Mini-Protean II, multi-screen, BioRad). Bound antibodies were detected using affinity purified rabbit anti-mouse IgG conjugated with peroxidase according to standard methods (ECL, Amersham).

Figure 6:
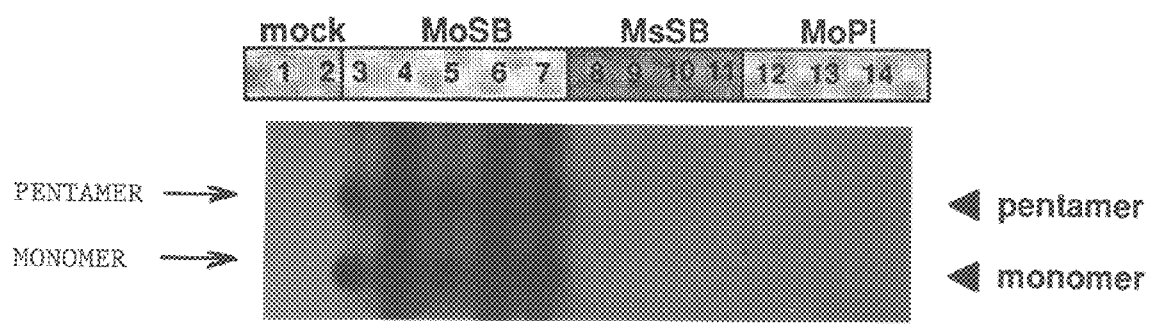

The results of this analysis are presented in FIG. 6. Sera from five of the five mice immunized with the CTB-recombinant poliovirus, MOSB (lanes 3–7), clearly contain IgG antibodies reactive with the CTB monomer and pentamer. Sera from mock-infected (lanes 1 and 2) or irrelevant control (MoPi, lanes 12–14), as expected, lack such specific antibodies. In addition, mice immunized with the Sabin-based recombinant CTB-expressing poliovirus did not show CTB-specific antibody reactivity (MsSB, lanes 8–11). A number of conclusions are suggested by these preliminary results. First, immunization with recombinant polioviruses can either directly generate or specifically prime an appropriate antibody response in immunized animals. The absence of CTB-specific antibodies in the sera of control mice, who were similarly immunized with purified CTB, and the IgG isotype of the CTB-reactive antibodies seen indicated that a memory response has been induced by vaccination. The reason for this is not clear, but may relate to the relative replicative characteristics of the recombinant polioviruses and may be resolvable by increasing the dose of recombinant virus vaccine. Both the wild type and recombinant Sabin polioviruses replicate less well than their wild-type Mahoney counterparts. Further, the transgenic mice used in these experiments do not support the efficient replication of the Sabin vaccine strains of poliovirus. Thus, limited replication in vivo may have prevented the generation of effective immunization by the Sabin-based recombinants.

Example 4
Evaluation of the Safety of the Recombinant Viruses

In parallel with the studies of the immunogenicity of recombinant polioviruses, preliminary studies were performed to evaluate the safety of the viruses. For these purposes, transgenic mice received intracerebral inoculation of equal titers ($5\times10^6$ pfu) of either the parental Mahoney (pathogenic) or Sabin (attenuated) strains, or their recombinant derivatives that express CTB. Although all mice inoculated with the Mahoney strain were paralyzed, none of the mice injected with recombinants experienced paralysis. This result suggests that the insertion of the CTB sequences within the poliovirus genome attenuates, rather than augments the pathogenicity of the resulting recombinant virus. A more detailed study of this phenomenon is in progress.

Example 5
Construction of Additional Replication Competent Polioviruses

The recombinant polioviruses represented schematically in FIG. 2 were constructed in a similar manner, using the methods and materials described herein (see Examples 1 and 2) and art-recognized methods. To explore the potential for expression of exogenous coding sequences at sites other than at the 5' of the recombinant poliovirus polyprotein, polylinker/proteolytic processing motifs were introduced at a number of additional locations within the viral genome. These sites include the junction between Vp1 and 2A (pMoV 2.1 and pMoV 2.2), the junction of 2A and 2B (pMoV 2.5), the junction of 2C and 3A (pMoV 3.1) and the junction of Vpg and 3C (pMoV 3.5). To facilitate processing of exogenous sequences within the interior of the viral polyprotein, appropriate proteolytic processing signals were included at both ends of the insert. When introduced in this manner, three of the novel sites for insertion permitted the generation of replication-competent recombinant viruses that stably carry the desired insert. The resulting viruses, shown in FIG. 2, designated pMoV 2.1, pMoV 2.2, pMoV 2.5 and pMoV 3.1 are all replication-competent, and in fact, display near wild-type plaque morphology and replicative kinetics. The only recombinant modification that resulted in abrogation of viral replication placed the inserted sequences at the junction of Vpg and 3C. The ability to insert exogenous antigenic sequences at at least four possible locations in the poliovirus genome permits flexibility in the derivation of recombinant poliovirus vaccines.

As shown in FIG. 2, vectors which include the 3C cleavage site and vectors which include the 2A cleavage site were constructed. Vectors that utilize the poliovirus 3C protease to release the exogenous sequences from the polyprotein precursor include the Q-G processing site. Analogous recombinant viruses that rely on the poliovirus 2A protease to effect appropriate processing of the recombinant polyprotein precursor include the characteristic 2A processing site provided by the Y-G pair and surrounding amino-acids. The viruses pMoV 2.1 and pMoV 2.2 in FIG. 2 represent such 2A-based vectors and as described above, display near wild-type growth. Poliovirus vectors (FIG. 2) were constructed that contain a more extensive polylinker sequence (EcoR1, Not1, BssH2 and Xho1) than present in the recombinant poliovirus represented in FIG. 1, to facilitate the ease of insertion of desired exogenous nucleic acid sequences into the recombinant vector. In addition, variants were also successfully derived that include a poly-glycine tract adjacent to the inserted sequence so as to enhance the structural flexibility of the region, and potentially increase the efficiency of proteolytic processing. In all, these vectors enhance the versatility of the basic strategy and provide a variety of alternative approaches for the generation of vaccine vectors.

An exogenous nucleic acid sequence or sequences, each encoding a protein or polypeptide to be expressed and a nucleic acid sequence or sequences, each encoding a proteolytic cleavage site (e.g., the 3C proteolytic site or the 2A proteolytic site) can be introduced into the parent poliovirus genome at any of these sites, using known methods and the methods described herein. The ability of the resulting recombinant polioviruses to produce the encoded protein(s) or polypeptide(s) can be assessed as described above. The immunogenicity of the recombinant polioviruses and their safety can also be assessed as described. (See Examples 3 and 4).

Example 6
Strategy for the Construction of a Recombinant Poliovirus

Examples 1–5 above utilize the insertion into the poliovirus genome of in-frame synthetic polylinkers containing restriction enzyme recognition sites. This Example 6 describes a strategy for the construction of a recombinant poliovirus which does not require the introduction of exogenous restriction sites or alteration of the flanking poliovirus genome around the insertion site for an exogenous gene. This Example 6 further describes a strategy for insertion of exogenous nucleic acid sequences in frame with the polyprotein open reading frame. Examples 7–9 below describe the insertion of specific exogenous nucleic acid sequences into this recombinant poliovirus so as to form a vector for expression of the exogenous polypeptides.

This Example 6 utilizes the system of Racaniello and Baltimore which allows genetic manipulation of poliovirus (Racaniello, V. R., and Baltimore, D., Science, 214:916–919 (1981)). Plasmids containing full-length cDNA copies of polio genomic RNA were found to produce infectious virus following transfection into appropriate host cells in culture. This system has been used to investigate many aspects of poliovirus replication, genetic stability and attenuation of vaccine strains.

Specifically, the poliovirus vector used is derived from the plasmid pLED3.2. The plasmid pLED3.2 consists of the plasmid pBR322 into which a full-length cDNA copy of the Sabin type 3 poliovirus genome has been inserted. The Sabin type 3 virus is an attenuated strain currently used in oral polio vaccines. The poliovirus cDNA is cloned behind a bacteriophage T7 RNA polymerase promoter. The presence of this promoter allows in vitro transcription using T7 RNA polymerase to form full-length RNA transcripts which produce poliovirus following transfection into tissue culture cells. Samples of the plasmid pLED3.2 were deposited with the American Type Culture Collection, 12301 Parklawn Drive, Rockville, Md. 20852, U.S.A., on Aug. 20, 1991, and were assigned accession number ATCC 75062.

The strategy for insertion of exogenous nucleic acid sequences in frame with the poliovirus polyprotein open reading frame involves the use of overlap extension polymerase chain reaction (PCR) (Horton, R. M., et al., Gene, 77:61–68 (1989)). This method allows fusion of gene sequences without the need for introduction of restriction sites. The exogenous genes are joined in frame with the polyprotein open reading frame without alteration of the flanking poliovirus sequence.

This strategy involves two rounds of PCR: The first introduces overlapping flanking sequences onto the gene to be cloned; the second uses two PCR fragments as template DNA and results in the exact fusion mediated by the overlapping sequences.

Expression clones are constructed using overlap extension PCR to fuse an exogenous gene at the start of the poliovirus polyprotein coding region (base 743). In addition, a sequence encoding the polio 3C protease recognition site is inserted 3' to the exogenous gene. The specific primers used in the Examples set forth below are described in Table 2.

TABLE 2

PRIMERS FOR CLONING OF
EXOGENOUS GENES INTO pLED3.2

| Primer | Direction | Sequence (5'-3') | | pLED3.2 Position |
|---|---|---|---|---|
| A | sense | CAGGATTTCAGTGTCACAATGGA GAACATCACATCAGGATTTCTAG GACC | (SEQ ID #7) | (725-745) |
| B | antisense | TACTTGAGCTCCTTGAAACAAAG CAATGTATACCCAA | (SEQ ID #8) | (757-746) |
| C | sense | ATCTTCGACGCGTTGCGCTC | (SEQ ID #9) | (270-289) |
| D | antisense | TGTGACACTGAAATCCTG | (SEQ ID #10) | (742-725) |
| E | sense | GCTTTGTTTCAAGGAGCTCAAGT ATCATCCCAA | (SEQ ID #11) | (746-764) |
| F | antisense | TCTTCCTAGGTAGTGGTAAT | (SEQ ID #12) | (1258-1239) |
| G | sense | GACAGGATTTCAGTGTCACAATG GGGCAGAAATCTTTCCACCAG-CAAT | (SEQ ID #13) | (723-745) |
| H | antisense | TTGTGGAATTCCACTGCATGGCC TGAGGATGAGTGTTTCTC | (SEQ ID #14) | |
| I | sense | GACAGGATTTCAGTGTCACAATG CAGTGGAATTCCACAACCTTCCA CCA | (SEQ ID #15) | (723-745) |
| J | antisense | CTGTGGAAGCGCCTTAATTAAGT TAACGCGGCCGCCCATTGTGACA CTGAAATC | (SEQ ID #16) | |
| K | sense | ATGGGCGGCCGCGTTAACTTAAT TAAGGCGCTTCCACAGGGAGCTC AAGTATCATCC | (SEQ ID #17) | |
| L | sense | TCACCTTCGTGGTAACCGCCAAC T | (SEQ ID #18) | (2871-2894) |
| M | antisense | CTGTGGAAGCGCCTTAATTAAGT TAACGCGGCCGCCATATGTGGTC AAACCTT | (SEQ ID #19) | |
| N | sense | TATGGCGGCCGCGTTAACTTAAT TAAGGCGCTTCCACAGGGCTTGG GCATCAGAATAA | (SEQ ID #20) | |
| O | antisense | ATCGTGCTGGTCACCATGCTG | (SEQ ID #21) | (3929-3909) |
| P | sense | CAGGATTTCAGTGTCACAATGTA CGGAATAGAATATACC | (SEQ ID #22) | (725-745) |
| Q | antisense | GCTCCTTGAAACAAAGCTACTCT GTAATAGAACGCTG | (SEQ ID #23) | (750-746) |

The first round PCR reactions contain approximately 2 ng template DNA, 100 pmol each primer, 200 μmol each dNTP, 10 mM KCl, 10 mM Tris-HCl, pH 8.3, 3.75 mM MgCl$_2$ and 5 units AMPLITAQ DNA polymerase, Stoffel Fragment (Perkin-Elmer/Cetus, Norwalk, Conn.). The reactions are set up in 100 μl volumes, overlaid with 40 μl light mineral oil. PCR cycling conditions are: 95° C. 2 minutes, ice 2 minutes, followed by 95° C. 1 minute, 50° C. 1 minute, 72° C. 2 minutes for 30 cycles. The resulting PCR fragments are purified using Promega's MAGIC PCR kit (Promega, Madison, Wis.) or by agarose gel electrophoresis (Sambrook, J., et al., *Molecular Cloning: A Laboratory Manual* (2nd Ed., Cold Spring Harbor Press, Cold Spring Harbor, N.Y. (1989)).

Regions of pLED3.2 which flank base 743 are also amplified in first round PCR reactions to provide the second template DNA to form the fusion. Additional overlapping sequences are not added onto these fragments; this permits the fragments to be used for the construction of a number of different fusions, each containing a different exogenous gene. The primers used for the region upstream (5') to base 743 are primers C and D (see Table 2). The primers used for the region downstream (3') to base 743 are primers E and F (see Table 2). The template for these reactions is pLED3.2, linearized with XbaI. The PCR reactions are conducted as described above. These reactions generate fragments of 472 base pairs and 524 base pairs for the 5' and 3' regions of pLED3.2, respectively. The resulting PCR fragments are purified on 0.8% low melting point agarose (SeaPlaque, FMC (Rockland, Me.)) and are then used as templates for subsequent reactions.

The second round PCR reactions involve mixing the two PCR fragments just described and performing the amplification in the presence of outside primers to yield the resulting fusion product. In the constructs to be described in Examples 7–11, the exogenous gene is fused with the 5' or 3' fragment in separate PCR reactions. The fusion products are then cloned into pLED3.2 using unique restriction sites present in that plasmid.

The second round PCR reactions contain 1 μl each template, 100 pmol each primer, 200 μmol each dNTP, 10 mM KCl, 10 mM Tris-HCl, pH 8.3, 3.75 mM $MgCl_2$ and 5 units AMPLITAQ DNA polymerase, Stoffel Fragment (Perkin-Elmer/Cetus). The reactions are set up in 100 μl volumes, overlaid with 40 μl light mineral oil. PCR cycling conditions for the second round reactions are: 94° C. 5 minutes, 72° C. 10 minutes, followed by 94° C. 1 minute, 50° C. 1 minute, 72° C. 2 minutes for 30 cycles. The fusion fragments are isolated on 0.8% low melting point agarose, digested with the appropriate restriction enzymes and subcloned into pLED3.2.

Example 7
Construction of a Recombinant Poliovirus Carrying the Hepatitis B Surface Antigen The poliovirus vector derived from the plasmid pLED3.2 as described in Example 6 is used for construction of a virus vector for expression of the S gene coding for the surface (S) antigen of hepatitis B virus. The S antigen has been found to be protective for the hepatitis B virus. The S antigen is a protein of 226 amino acids in length. In this Example, the hepatitis B S gene is derived from subtype ayw of the human virus, specifically from cloned genomic DNA. The hepatitis B S gene from subtype ayw is 675 base pairs in length (Galiber, F., et al., *Nature*, 281:646–650 (1979)).

Primers A and B (see Table 2) are used in the first round of PCR to amplify the S gene and incorporate overlapping pLED3.2 sequences into the PCR product. The underlined sequences in these two primers correspond to sequence in pLED3.2, with the remaining sequence corresponding to the S gene. In primer A, the S gene sequence corresponds to the initiation codon for the S antigen at base pair 157 in the hepatitis B genome. The antisense primer B encodes the carboxyl terminus of the S antigen plus the recognition site for the polio 3C protease. These primers are used with cloned hepatitis B DNA as a template to generate a PCR fragment of 717 base pairs. The first round PCR cycling conditions differ from those described in Example 6 as follows: 94° C. 2 minutes, ice 2 minutes, followed by 94° C. 1 minute, 26° C. 1 minute, 70° C. 2 minutes for 10 cycles, 94° C. 1 minute, 45° C. 1 minute, 70° C. 2 minutes for 20 cycles.

A second PCR reaction uses the PCR fragments described above to generate fusions between pLED3.2 flanking regions and the S gene. Two PCR reactions are performed with either the 5' LED3.2 flanking region or the 3' LED3.2 flanking region plus the S gene PCR fragment as template. The sense primer for the 5' fusion is primer C, which primes at the 5' end of the pLED3.2 flanking region. The antisense primer B primes at the 3' end of the S gene. For the 3' fusion, the sense primer is the S gene sense primer (A), with the 3' LED3.2 antisense primer (F). The resulting PCR fragments are 1175 and 1222 base pairs for the 5' and 3' fusions, respectively. The fusion fragments are then purified by agarose gel electrophoresis.

The fusion fragments resulting from the second round PCR reactions are then digested with restriction enzymes for final construction of the poliovirus vector containing the S gene. The 5' LED3.2-S gene fusion is digested with MluI and BstXI (a unique site within the S gene). The 3' LED3.2-S gene fusion is digested with AvrII and BstXI. The plasmid pLED3.2 is digested at base pair 278 with MluI and is digested at base pair 1249 with AvrII to remove a 971 base pair fragment. Following purification by 0.8% agarose gel electrophoresis, the resulting digests are mixed and ligated together using standard methods (Sambrook, et al., supra) to form pLED3.2/HBV. The DNA sequence of this full length polio-fusion construct is determined using an Applied Biosystems (Foster City, Calif.) 370A DNA sequencer.

Next, transcription and transfection reactions are conducted. RNA transcripts generated from the T7 promoter are transfected into Vero cells to generate infectious poliovirus. For these experiments, approximately 5 μg pLED3.2/HBV are prepared for generation of RNA transcripts by digestion of the plasmid with PvuI. PvuI digestion results in two fragments, with the larger fragment containing the T7 promoter followed by the full-length polio genome containing the S gene fusion. The digestion reaction is phenol extracted and ethanol precipitated. The precipitated DNA is resuspended in 20 p1 water. Full-length RNA transcripts are synthesized in vitro from the PvuI-digested DNA using T7 RNA polymerase (Moss, E. G., et al., *J. Virol.*, 63:1884–1890 (1989)). Transcription products are analyzed by agarose gel electrophoresis.

Confluent 25 $cm^2$ Vero cell monolayers are transfected with transcripts using DEAE-transfection protocol (Van der Werf, S., *Proc. Natl. Acad. Sci., U.S.A.*, 83:2330–2334 (1986)). Approximately 25 μg RNA are mixed with DEAE-dextran (0.5 mg/ml) and then overlaid onto Vero cells. Following 30 minutes incubation at room temperature, the inoculum is removed and cells are washed. Fresh modified Earle's lactal maintenance medium is added and cells incubated at 33.5° C. Following 5 days of incubation, the total cytopathic effect (lysis of cells in monolayer) is observed and replication competent recombinant viral poliovirus is harvested from the culture media.

Viral stocks containing recombinant poliovirus generated from the construct pLED3.2/HBV are titered by plaque assay on Vero cells. In addition, RNA is extracted from recombinant virus and analyzed by reverse transcription and PCR using the GENEAMP THERMOSTABLE rTth Reverse Transcriptase RNA PCR Kit (Perkin-Elmer/Cetus). The results demonstrate that the S gene is stably maintained in the recombinant pLED3.2/HBV virus through passage in culture.

A variety of methods are used to analyze the expression of the S antigen from the poliovirus vector. These methods, which are standard procedures, include immunoperoxidase staining of infected cells, immunoprecipitation of viral and foreign proteins, Western blots and Dot blots (Coligan, J. E., et al., eds., *Current Protocols in Immunology*, John Wiley and Sons (1992)).

An immunoperoxidase staining assay is used for detection of proteins in virus-infected Vero cells. Vero cells are infected with virus and fixed with ethanol or methanol at various times post-infection. The fixed cell monolayer is incubated with antisera against either poliovirus proteins or S antigen. The plates are washed and then incubated with a secondary antibody (such as goat antirabbit IgG) conjugated to Horse Radish Peroxidase (HRP). The plates are again washed and then an HRP substrate, 3,3'-diaminobenzidine tetrahydrochloride (Sigma, St. Louis, Mo.) is added. Cells which express proteins that cross-react with the antibodies are stained.

Vero cell monolayers are infected with recombinant virus. Cell lysates can be examined by immunoprecipitation or Western blotting for the presence of viral encoded proteins. For immunoprecipitation, cell lysates are incubated with antisera against poliovirus or the exogenous protein. Protein A Sepharose (Sigma, St. Louis, Mo.) is then added to the mixture and incubated further. The Sepharose beads are centrifuged, washed and eluted with SDS dissociation buffer. The precipitated proteins can be analyzed by SDS-polyacrylamide gel electrophoresis. For Western blotting, the cell lysates are separated by SDS-PAGE, transferred to nitrocellulose and incubated with antisera to the proteins of interest. The blots are washed, incubated with a secondary antibody (such as goat anti-rabbit IgG) conjugated to HRP. The blots are washed again and then an HRP substrate, 4-chloro-1-naphthol (Bio-Rad, Richmond, Calif.) plus hydrogen peroxide, is added to identify the cross-reacting proteins.

In this Example 7 and in the succeeding Examples, the method described in Example 3 above using transgenic mice may be used to assess the immunogenicity of the recombinant poliovirus and the exogenous polypeptide.

Example 8
Construction of a Recombinant Poliovirus Carrying the Henatitis B pre-S Region Genes The envelope of the hepatitis B virus contains three proteins that are all encoded within the S gene region of the hepatitis B genome. Each antigen is encoded by a different start site within the open reading frame of the S gene region. The major protein is the S antigen which is 226 amino acids in length. The two other proteins are the middle and large proteins which are encoded by the pre-S1 and pre-S2 genes, respectively (Tiollais, P., et al., Nature, 317:489–495 (1985)). It is believed that inclusion of the pre-S1 and/or pre-S2 antigens in a vaccine, which may further contain the S antigen, may increase the efficacy of hepatitis B vaccines.

The strategy for constructing poliovirus vectors containing the pre-S1 or pre-S2 genes is similar to that described in Example 7 for the S gene. Primers are designed to amplify each gene and to introduce poliovirus flanking sequences at each end of the gene. The primers are set forth in Table 2. PCR reactions and cycling conditions are as described above.

Primers G and H are used for amplification of the pre-S1 region from hepatitis B DNA. Primer G introduces poliovirus sequence (underlined in Table 2) at the 5' end of the pre-S1 gene, with pre-S1 sequence beginning at base 2580 in the hepatitis B genome. The antisense primer H is located in the pre-S region of the genome (common to both per-S1 and pre-S2) from base 3152-6 and includes an EcoRI site at base 1. PCR amplification of cloned hepatitis B genomic DNA with primers G and H results in a 338 base pair fragment. This fragment is used as template DNA, together with the 5' LED3.2 fragment (from primers C and D described in Example 6) in a second PCR reaction. Amplification with primers C and H results in a fused 5' LED3.2-pre-S1 fragment of 770 base pairs. For construction of the 3' end of the per-S1 gene, the PCR-fragment 3LED3.2/pre-S2 is used (see next paragraph), because this region is the same in both pre-S constructs. The 5' LED3.2-pre-S1 fragment is digested with MluI and EcoRI. The 3' LED3.2-pre-S2 fragment is digested with EcoRI and AvrII. The resulting fragments are purified by agarose gel electorphoresis and ligated into pLED3.2 which had been digested with MluII and AvrII. The resulting construct is designated pLED3.2/pre-S1.

Following the procedures of Example 7, the DNA sequence of this full length polio-fusion construct is determined using an Applied Biosystems 370A DNA sequencer.

Next, transcription and transfection reactions are conducted. RNA transcripts generated from the T7 promoter are transfected into Vero cells to generate infectious poliovirus. For these experiments, approximately 5 μg pLED3.2/per-S1 is prepared for generation of RNA transcripts by digestion of the plasmid with PvuI. PvuI digestion results in two fragments, with the larger fragment containing the T7 promoter followed by the full-length polio genome containing the per-S1 gene fusion. The digestion reaction is phenol extracted and ethanol precipitated. The precipitated DNA is resuspended in 20 μl water. Full-length RNA transcripts are synthesized in vitro from the PvuI-digested DNA using T7 RNA polymerase. Transcription products are analyzed by agarose gel electrophoresis.

Confluent 25 cm$^2$ Vero cell monolayers are transfected with transcripts using DEAE-transfection protocol. Approximately 25 μg RNA is mixed with DEAE-dextran (0.5 mg/ml) and then overlaid onto Vero cells. Following 30 minutes incubation at room temperature, the inoculum is removed and cells are washed. Fresh modified Earle's lactal maintenance medium is added and cells incubated at 33.5° C. Cultures are incubated until total cytopathic effect is observed and recombinant poliovirus is harvested from the culture media.

Viral stocks containing recombinant poliovirus generated from the construct pLED3.2/per-S1 are titered by plaque assay on Vero cells. In addition, RNA is extracted from recombinant virus and analyzed by reverse transcription and PCR using the GENEAMP THERMOSTABLE rTth Reverse Transcriptase RNA PCR Kit (Perkin-Elmer/Cetus). The results demonstrate that the pre-S1 gene is stably maintained in the recombinant pLED3.2/per-S1 virus through passage in culture.

A variety of methods are used to analyze the expression of the per-S1 antigen from the poliovirus vector. These methods include immunoperoxidase staining of infected cells, immunoprecipitation of viral and foreign proteins, Western blots and Dot blots.

The expression clone for pre-S2 uses primer I as the sense primer and primer B as the antisense primer (see Table 2). These primers result in amplification of the entire pre-S2 gene and introduce LED3.2 sequences at both the 5' and 3' ends. The PCR reaction generates an 867 base pair fragment. Following purification, this fragment is used as a template for the second round PCR reactions with either the 5' LED3.2 or 3' LED3.2 fragments, resulting in the formation of fusion products designated 5' LED3.2/pre-S2 and 3' LED3.2/pre-S2. The primers used for the second round PCR are C and B for the 5' fusion and I and F for the 3' fusion. The 5' LED3.2/pre-S2 fragment is digested with MluI and XbaI. The 3' LED3.2/pre-S2 fragment is digested with XbaI and AvrII. The resulting fragments are purified by agarose gel electrophoresis and ligated into pLED3.2 which had been digested with MluI and AvrII. The resulting construct is designated pLED3.2/pre-S2.

Following the procedures of Example 7, the DNA sequence of this full length polio-fusion construct is determined using an Applied Biosystems 370A DNA sequencer.

Next, transcription and transfection reactions are conducted. RNA transcripts generated from the T7 promoter are transfected into Vero cells to generate infectious poliovirus. For these experiments, approximately 5 μg pLED3.2/pre-S2 is prepared for generation of RNA transcripts by digestion of the plasmid with PvuI. PvuI digestion results in two fragments, with the larger fragment containing the T7 promoter followed by the full-length polio genome containing the pre-S2 gene fusion. The digestion reaction is phenol extracted and ethanol precipitated. The precipitated DNA is resuspended in 20 μl water. Full-length RNA transcripts are synthesized in vitro from the PvuI-digested DNA using T7 RNA polymerase. Transcription products are analyzed by agarose gel electrophoresis.

Confluent 25 cm$^2$ Vero cell monolayers are transfected with transcripts using DEAE-transfection protocol. Approximately 25 μg RNA is mixed with DEAE-dextran (0.5mg/ml) and then overlaid onto Vero cells. Following 30 minutes incubation at room temperature, the inoculum is removed and cells are washed. Fresh modified Earle's lactal maintenance medium is added and cells incubated at 33.5° C. Cultures are incubated until total cytopathic effect is observed and recombinant poliovirus is harvested from the culture media.

Viral stocks containing recombinant poliovirus generated from the construct pLED3.2/pre-S2 are titered by plaque assay on Vero cells. In addition, RNA is extracted from recombinant virus and analyzed by reverse transcription and PCR using the GENEAMP THERMOSTABLE rTth Reverse Transcriptase RNA PCR Kit (Perkin-Elmer/Cetus). The results demonstrate that the pre-S2 gene is stably maintained in the recombinant pLED3.2/pre-S2 virus through passage in culture.

A variety of methods are used to analyze the expression of the pre-S2 antigen from the poliovirus vector. These methods include immunoperoxidase staining of infected cells, immunoprecipitation of viral and foreign proteins, Western blots and Dot blots.

For both per-S1 and pre-S2, an immunoperoxidase staining assay is used for detection of proteins in virus-infected Vero cells. Vero cells are infected with virus and fixed with ethanol or methanol at various times post-infection. The fixed cell monolayer is incubated with antisera against either poliovirus proteins or the pre-S1 antigen or the pre-S2 antigen, as the case may be. The plates are washed and then incubated with a secondary antibody (such as goat anti-rabbit IgG) conjugated to HRP. The plates are again washed and then an HRP substrate, 3,3'-diaminobenzidine tetrahydrochloride (Sigma, St. Louis, Mo.) is added. Cells which express proteins that cross-react with the antibodies are stained.

Vero cell monolayers are infected with recombinant virus. Cell lysates can be examined by immunoprecipitation or Western blotting for the presence of viral encoded proteins. For immunoprecipitation, cell lysates are incubated with antisera against poliovirus or the exogenous protein. Protein A Sepharose (Sigma, St. Louis, Mo.) is then added to the mixture and incubated further. The Sepharose beads are centrifuged, washed and eluted with SDS dissociation buffer. The precipitated proteins can be analyzed by SDS-polyacrylamide gel electrophoresis. For Western blotting, the cell lysates are separated by SDS-PAGE, transferred to nitrocellulose and incubated with antisera to the proteins of interest. The blots are washed, incubated with a secondary antibody (such as goat anti-rabbit IgG) conjugated to HRP. The blots are washed again and then an HRP substrate, 4-chloro-1-naphthol (Bio-Rad, Richmond, Calif.) plus hydrogen peroxide, is added to identify the cross-reacting proteins.

Example 9

Construction of a Recombinant Poliovirus Carrying the Rotavirus VP7 Gene

An expression clone designated pLED3.2/VP7 is constructed wherein the gene encoding the rotavirus VP7 antigen is inserted into the poliovirus genome. The clone contains the full-length gene for VP7, which is approximately 1 kilobase in length. The clone is constructed using overlap extension PCR and the gene inserted at the start of the poliovirus open reading frame (base 743). The primers used for the first round PCR are P and Q (Table 2). The template DNA is a plasmid clone containing the full-length rotavirus VP7 gene. The PCR product from this amplification is 1012 base pairs in length. The PCR cycling conditions for the first round reaction differ from the standard conditions described in Example 6 as follows: 94° C. 2 minutes, ice 2 minutes, followed by 94° C. 1 minute, 26° C. 1 minute, 70° C. 2 minutes for 10 cycles, 94° C. 1 minute, 45° C. 1 minute, 70° C. 2 minutes for 20 cycles.

The second round PCR reactions are performed as described above. The first round PCR fragment is mixed with either 5' LED3.2 or 3' LED3.2 and amplified with primers C and Q for the 5' fusion or P and F for the 3' fusion. The resulting fusion products are digested with MluI and BglII for the 5' fusion or BglII and AvrII for the 3' fusion. These digestion products are then subcloned into pLED3.2 to form pLED3.2/VP7.

The DNA sequence of this full length polio-fusion construct is determined using an Applied Biosystems (Foster City, Calif.) 370A DNA sequencer.

Next, transcription and transfection reactions are conducted. RNA transcripts generated from the T7 promoter are transfected into Vero cells to generate infectious poliovirus. For these experiments, approximately 5 $\mu$g pLED3.2/VP7 are prepared for generation of RNA transcripts by digestion of the plasmid with PvuI. PvuI digestion results in two fragments, with the larger fragment containing the T7 promoter followed by the full-length polio genome containing the VP7 gene fusion. The digestion reaction is phenol extracted and ethanol precipitated. The precipitated DNA is resuspended in 20 $\mu$l water. Full-length RNA transcripts are synthesized in vitro from the PvuI-digested DNA using T7 RNA polymerase (Moss, E. G., et al., *J. Virol.*, 63:1884–1890 (1989)). Transcription products are analyzed by agarose gel electrophoresis.

Confluent 25 $cm^2$ Vero cell monolayers are transfected with transcripts using DEAE-transfection protocol (Van der Werf, S., *Proc. Natl. Acad. Sci., U.S.A.*, 83:2330–2334 (1986)). Approximately 25 $\mu$g RNA are mixed with DEAE-dextran (0.5 mg/ml) and then overlaid onto Vero cells. Following 30 minutes incubation at room temperature, the inoculum is removed and cells are washed. Fresh modified Earle's lactal maintenance medium is added and cells incubated at 33.5° C. Cultures are incubated until total cytopathic effect is observed and recombinant poliovirus is harvested from the culture media.

Viral stocks containing recombinant poliovirus generated from the construct pLED3.2/VP7 are titered by plaque assay on Vero cells. In addition, RNA is extracted from recombinant virus and analyzed by reverse transcription and PCR using the GENEAMP THERMOSTABLE rTth Reverse Transcriptase RNA PCR Kit (Perkin-Elmer/Cetus). The results demonstrate that the VP7 gene is stably maintained in the recombinant pLED3.2/VP7 virus through passage in culture.

A variety of methods are used to analyze the expression of VP7 from the poliovirus vector. These methods, which are standard procedures, include immunoperoxidase staining of infected cells, immunoprecipitation of viral and foreign proteins, Western blots and Dot blots (Coligan, J. E., et al., eds., *Current Protocols in Immunology*, John Wiley and Sons (1992)).

An immunoperoxidase staining assay is used for detection of proteins in virus-infected Vero cells. Vero cells are infected with virus and fixed with ethanol or methanol at various times post-infection. The fixed cell monolayer is incubated with antisera against either poliovirus proteins or VP7. The plates are washed and then incubated with a secondary antibody (such as goat anti-rabbit IgG) conjugated to Horse Radish Peroxidase (HRP). The plates are again washed and then an HRP substrate, 3,3'-diaminobenzidine tetrahydrochloride (Sigma, St. Louis, Mo.) is added. Cells which express proteins that cross-react with the antibodies are stained.

Vero cell monolayers are infected with recombinant virus. Cell lysates can be examined by immunoprecipitation or Western blotting for the presence of viral encoded proteins. For immunoprecipitation, cell lysates are incubated with antisera against poliovirus or the exogenous protein. Protein A Sepharose (Sigma, St. Louis, Mo.) is then added to the mixture and incubated further. The Sepharose beads are centrifuged, washed and eluted with SDS dissociation buffer. The precipitated proteins can be analyzed by SDS-polyacrylamide gel electrophoresis. For Western blotting, the cell lysates are separated by SDS-PAGE, transferred to nitrocellulose and incubated with antisera to the proteins of interest. The blots are washed, incubated with a secondary antibody (such as goat anti-rabbit IgG) conjugated to HRP. The blots are washed again and then an HRP substrate, 4-chloro-1-naphthol (Bio-Rad, Richmond, Calif.) plus hydrogen peroxide, is added to identify the cross-reacting proteins.

Example 10
Construction of Poliovirus Polylinker Cassette Vectors

The exogenous genes may also be inserted into the poliovirus genome through the construction of two poliovirus cloning vectors akin to those described in Examples 1–5, in that each vector incorporates unique restriction enzyme cloning sites, each at a different location within the poliovirus genome. This polyliner cassette vector methodology provides a simpler cloning procedure than the method of Example 6, although the latter limits the addition of additional amino acids not found in the original exogenous polypeptide.

The first vector (vector 1) contains the polylinker cassette in-frame with the poliovirus polyprotein immediately following the initiation codon AUG at base 743. The following restriction sites are then introduced: NotI, HpaI and PacI. These are followed immediately by the sequence encoding the polio 3C protease recognition site. This sequence is then adjusted by the addition or deletion of 1–2 extra bases to maintain the correct open reading frame throughout this region.

Overlap extension PCR is used to introduce the restriction sites during the construction of the vectors. In order to construct vector 1, primers J and K (Table 2) are synthesized to introduce the polylinker cassette at base 743. The first round PCR reactions used pLED3.2 as template DNA, primers C and J for the 5' region, and primers K and F for the 3' region. The expected sizes for the amplified fragments are 512 and 551 base pairs for the 5' and 3' regions, respectively. These fragments are used directly from the PCR reaction to serve as the template for the second round PCR with primers C and F. The resulting fragment is 1016 base pairs in length and contains the polylinker sequence and 3C protease recognition site in the middle of the fragment. The fragment is purified, digested with MluI and AvrII and subcloned into pLED3.2, which had been digested with the same restriction enzymes.

Proteolytic processing of the poliovirus polyprotein occurs in multiple steps during viral replication. Initial proteolytic cleavage is produced by the 2A protease, resulting in the formation of proteins designated P1 and P2–P3. Each of these is further cleaved by the 3C protease to produce the individual viral proteins. During the proteolytic processing of the polyprotein, partial cleavage products have been shown to have distinct functions from the final cleavage products (Harris, K. S., et al., Semin. Virol., 1:323–333 (1990)). Insertion of an exogenous gene into the polyprotein at regions encoding functional precursors will not generate viable virus. The second cassette vector is designed to introduce restriction sites at the junction between P1 and P2 (base 3377).

The restriction sites introduced are NotI, HpaI and PacI. There is a 2A protease recognition site 5' to these restriction sites; a 3C protease recognition site is introduced 3' to these sites. The first round PCR reactions use pLED3.2 as template DNA, primers L and M for the 5' region, and primers N and O for the 3' region (Table 2).

The expected sizes for the amplified fragments are 563 and 592 bp for the 5' and 3', respectively. These fragments are used directly from the PCR reaction to serve as the template for the second round PCR with primers L and O. The resulting fragment is 1096 bp in length and contains the 2A protease recognition site, polylinker sequence and 3C protease recognition site in the middle. The fragment is then digested with BstEII and subcloned into pLED3.2 digested with the same enzyme.

The cassette vectors are used as expression vectors for exogenous genes. Exogenous genes are cloned into the cassette vectors either using existing compatible restriction sites or through the addition of those restriction sites to the ends of the gene by PCR. In the latter case, the exogenous gene is amplified by PCR using primers corresponding to the 5' and 3' ends of the gene. When these primers are synthesized, a restriction site is added to the 5' end of the sense primer and a second restriction site is added to the 5' end of the antisense primer. Following amplification of the gene in a standard PCR reaction, the resulting PCR fragment will have the gene flanked by the two restriction sites. The vector and the PCR fragment are both digested with the two restriction enzymes and then ligated together, resulting in the expression clone of interest.

It is to be noted that the primers can be designed such that they correspond to any region of the exogenous gene of interest, such that partial genes could be incorporated into the vector. Furthermore, digestion of the vector with HpaI results in a blunt-ended fragment. Therefore, any blunt fragment of an exogenous gene could be cloned into the vector.

Example 11
Construction of a Recombinant Poliovirus Carrying the *B. pertussis* 69 kD Outer Membrane Protein Gene The poliovirus cassette vectors of Example 10 are used to express the 69 kD outer membrane protein of *B. pertussis*. The mature protein is encoded within a region of the gene of approximately 1.8 kb. This region or shorter regions of the open reading frame can be amplified by PCR with sequence specific primers. The primers are designed to contain a NotI site at the 5' end of the sense primer and a PacI site at the 5' end of the antisense primer. The primers must also be adjusted so that the open reading frame and poliovirus 3C protease recognition site are in frame. Following amplification by PCR, the resulting fragment is purified by agarose gel electrophoresis or with a MAGIC PCR kit (Promega), digested with NotI and PacI, and ligated into the vector restricted with the same enzymes. The resulting plasmid is designated pLED3.2/69 kD. The DNA sequence of this full length polio-fusion construct is determined using an Applied Biosystems (Foster City, Calif.) 370A DNA sequencer.

Next, transcription and transfection reactions are conducted. RNA transcripts generated from the T7 promoter are transfected into Vero cells to generate infectious poliovirus. For these experiments, approximately 5 μg pLED3.2/69 kD are prepared for generation of RNA transcripts by digestion of the plasmid with PvuI. PvuI digestion results in two fragments, with the larger fragment containing the T7 promoter followed by the full-length polio genome containing the 69 kD gene fusion. The digestion reaction is phenol extracted and ethanol precipitated. The precipitated DNA is resuspended in 20 μl water. Full-length RNA transcripts are synthesized in vitro from the PvuI-digested DNA using T7 RNA polymerase (Moss, E. G., et al., *J. Virol.*, 63:1884–1890 (1989)). Transcription products are analyzed by agarose gel electrophoresis.

Confluent 25 $cm^2$ Vero cell monolayers are transfected with transcripts using DEAE-transfection protocol (Van der Werf, S., *Proc. Natl. Acad. Sci., U.S.A.*, 83:2330–2334 (1986)). Approximately 25 μg RNA are mixed with DEAE-dextran (0.5 mg/ml) and then overlaid onto Vero cells. Following 30 minutes incubation at room temperature, the inoculum is removed and cells are washed. Fresh modified Earle's lactal maintenance medium is added and cells incubated at 33.5° C. Cultures are incubated until total cytopathic effect is observed and recombinant poliovirus is harvested from the culture media.

Viral stocks containing recombinant poliovirus generated from the construct pLED3.2/69 kD are titered by plaque assay on Vero cells. In addition, RNA is extracted from recombinant virus and analyzed by reverse transcription and PCR using the GENEAMP THERMOSTABLE rTth Reverse Transcriptase RNA PCR Kit (Perkin-Elmer/Cetus). The results demonstrate that the 69 kD gene is stably maintained in the recombinant pLED3.2/69 kD virus through passage in culture.

A variety of methods are used to analyze the expression of the 69 kD outer membrane protein from the poliovirus vector. These methods, which are standard procedures, include immunoperoxidase staining of infected cells, immunoprecipitation of viral and foreign proteins, Western blots and Dot blots (Coligan, J. E., et al., eds., *Current Protocols in Immunology*, John Wiley and Sons (1992)).

An immunoperoxidase staining assay is used for detection of proteins in virus-infected Vero cells. Vero cells are infected with virus and fixed with ethanol or methanol at various times post-infection. The fixed cell monolayer is incubated with antisera against either poliovirus proteins or 69 kD outer membrane protein. The plates are washed and then incubated with a secondary antibody (such as goat anti-rabbit IgG) conjugated to Horse Radish Peroxidase (HRP). The plates are again washed and then an HRP substrate, 3,3'-diaminobenzidine tetrahydrochloride (Sigma, St. Louis, Mo.) is added. Cells which express proteins that cross-react with the antibodies are stained.

Vero cell monolayers are infected with recombinant virus. Cell lysates can be examined by immunoprecipitation or Western blotting for the presence of viral encoded proteins. For immunoprecipitation, cell lysates are incubated with antisera against poliovirus or the exogenous protein. Protein A Sepharose (Sigma, St. Louis, Mo.) is then added to the mixture and incubated further. The Sepharose beads are centrifuged, washed and eluted with SDS dissociation buffer. The precipitated proteins can be analyzed by SDS-polyacrylamide gel electrophoresis. For Western blotting, the cell lysates are separated by SDS-PAGE, transferred to nitrocellulose and incubated with antisera to the proteins of interest. The blots are washed, incubated with a secondary antibody (such as goat anti-rabbit IgG) conjugated to HRP. The blots are washed again and then an HRP substrate, 4-chloro-1-naphthol (Bio-Rad, Richmond, Calif.) plus hydrogen peroxide, is added to identify the cross-reacting proteins.

Example 12

Construction of a Recombinant Poliovirus Carrying the Herpes Simplex Glycoprotein D Gene The poliovirus cassette vectors of Example 10 are used to express glycoprotein D of herpes simplex virus. The protein is encoded by a gene of approximately 1.2 kb. This region or shorter regions of the open reading frame can be amplified by PCR with sequence specific primers. The primers are designed to contain a NotI site at the 5' end of the sense primer and a PacI site at the 5' end of the antisense primer. The primers must also be adjusted so that the open reading frame and poliovirus 3C protease recognition site are in frame. Following amplification by PCR, the resulting fragment is purified by agarose gel electrophoresis or with a MAGIC PCR kit (Promega), digested with NotI and PacI, and ligated into the vector restricted with the same enzymes. The resulting plasmid is designated pLED3.2/gD. The DNA sequence of this full length polio-fusion construct is determined using an Applied Biosystems (Foster City, Calif.) 370A DNA sequencer.

Next, transcription and transfection reactions are conducted. RNA transcripts generated from the T7 promoter are transfected into Vero cells to generate infectious poliovirus. For these experiments, approximately 5 μg PLED3.2/gD are prepared for generation of RNA transcripts by digestion of the plasmid with PvuI. PvuI digestion results in two fragments, with the larger fragment containing the T7 promoter followed by the full-length polio genome containing the gD gene fusion. The digestion reaction is phenol extracted and ethanol precipitated. The precipitated DNA is resuspended in 20 μl water. Full-length RNA transcripts are synthesized in vitro from the PvuI-digested DNA using T7 RNA polymerase (Moss, E. G., et al., *J. Virol.*, 63:1884–1890 (1989)). Transcription products are analyzed by agarose gel electrophoresis.

Confluent 25 $cm^2$ Vero cell monolayers are transfected with transcripts using DEAE-transfection protocol (Van der Werf, S., *Proc. Natl. Acad. Sci., U.S.A.*, 83:2330–2334 (1986)). Approximately 25 μg RNA are mixed with DEAE-dextran (0.5 mg/ml) and then overlaid onto Vero cells. Following 30 minutes incubation at room temperature, the inoculum is removed and cells are washed. Fresh modified Earle's lactal maintenance medium is added and cells incubated at 33.5° C. Cultures are incubated until total cytopathic effect is observed and recombinant poliovirus is harvested from the culture media.

Viral stocks containing recombinant poliovirus generated from the construct pLED3.2/gD are titered by plaque assay on Vero cells. In addition, RNA is extracted from recombinant virus and analyzed by reverse transcription and PCR using the GENEAMP THERMOSTABLE rTth Reverse Transcriptase RNA PCR Kit (Perkin-Elmer/Cetus). The results demonstrate that the gD gene is stably maintained in the recombinant pLED3.2/gD virus through passage in culture.

A variety of methods are used to analyze the expression of gD from the poliovirus vector. These methods, which are standard procedures, include immunoperoxidase staining of infected cells, immunoprecipitation of viral and foreign proteins, Western blots and Dot blots (Coligan, J. E., et al., eds., *Current Protocols in Immunoloqy*, John Wiley and Sons (1992)).

An immunoperoxidase staining assay is used for detection of proteins in virus-infected Vero cells. Vero cells are infected with virus and fixed with ethanol or methanol at various times post-infection. The fixed cell monolayer is incubated with antisera against either poliovirus proteins or gD. The plates are washed and then incubated with a secondary antibody (such as goat anti-rabbit IgG) conjugated to Horse Radish Peroxidase (HRP). The plates are again washed and then an HRP substrate, 3,3'-diaminobenzidine tetrahydrochloride (Sigma, St. Louis, Mo.) is added. Cells which express proteins that cross-react with the antibodies are stained.

Vero cell monolayers are infected with recombinant virus. Cell lysates can be examined by immunoprecipitation or Western blotting for the presence of viral encoded proteins. For immunoprecipitation, cell lysates are incubated with antisera against poliovirus or the exogenous protein. Protein A Sepharose (Sigma, St. Louis, Mo.) is then added to the mixture and incubated further. The Sepharose beads are centrifuged, washed and eluted with SDS dissociation buffer. The precipitated proteins can be analyzed by SDS-polyacrylamide gel electrophoresis. For Western blotting, the cell lysates are separated by SDS-PAGE, transferred to nitrocellulose and incubated with antisera to the proteins of interest. The blots are washed, incubated with a secondary antibody (such as goat anti-rabbit IgG) conjugated to HRP. The blots are washed again and then an HRP substrate, 4-chloro-1-naphthol (Bio-Rad, Richmond, Calif.) plus hydrogen peroxide, is added to identify the cross-reacting proteins.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A replication-competent recombinant poliovirus which expresses an exogenous polypeptide as a component of a recombinant polyprotein precursor that is proteolytically processed, with the result that the exogenous polypeptide is released from the recombinant polyprotein precursor, in which the recombinant genome comprises:
   a) an exogenous nucleic acid sequence encoding an exogenous polypeptide to be expressed;
   b) an exogenous sequence which is a polioviral proteolytic cleavage site and which is cleaved by a poliovirus protease, wherein the protease proteolytically processes a protein precursor produced by a parent poliovirus modified to make the recombinant poliovirus; and
   c) the genome of the parent poliovirus modified to make the recombinant poliovirus,
wherein (a) and (b) are inserted in (c) at a location in the genome of the parent poliovirus such that they do not disrupt a polioviral sequence necessary for polioviral replication and when expressed, the exogenous polypeptide is expressed as a component of the polyprotein precursor produced by the recombinant poliovirus, the polyprotein precursor is proteolytically processed by the recombinant poliovirus and the exogenous polypeptide is not included in a mature poliovirus particle produced by the replication-competent poliovirus.

2. A replication-competent recombinant poliovirus which expresses an exogenous polypeptide as a component of a recombinant polyprotein precursor that is proteolytically processed, with the result that the exogenous polypeptide is released from the recombinant polyprotein precursor, in which the recombinant genome comprises:
   a) an exogenous nucleic acid sequence encoding an exogenous polypeptide to be expressed;
   b) an exogenous sequence which is a polioviral proteolytic cleavage site for the poliovirus 3C protease or for the poliovirus 2A protease; and
   c) the genome of a parent poliovirus,
wherein the exogenous nucleic acid sequence of (a) and nucleic acid sequence encoding an artificial proteolytic cleavage site for the poliovirus 3C protease or the poliovirus 2A protease of (b) are present in the recombinant poliovirus genome in the following order: 5' untranslated region of the poliovirus genome—unique poliovirus start codon—exogenous nucleic acid sequence of (a)—nucleic acid sequence encoding the artificial proteolytic cleavage site of (b)—second codon of the parent poliovirus genome—remainder of the parent poliovirus genome and when expressed, the exogenous polypeptide is expressed as a component of the polyprotein precursor produced by the recombinant poliovirus, the polyprotein precursor is proteolytically processed by the recombinant poliovirus and the exogenous polypeptide is not included in a mature poliovirus particle produced by the replication-competent poliovirus.

3. The replication-competent recombinant poliovirus of claim 2 wherein the nucleic acid sequence of (a) encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

4. The replication-competent recombinant poliovirus of claim 2 wherein the exogenous nucleic acid sequence of (a) encodes a polypeptide antigen and the genome of the parent poliovirus is the genome of a Sabin poliovirus.

5. The replication-competent recombinant poliovirus of claim 4 wherein the Sabin poliovirus is selected from the group consisting of: Sabin poliovirus type 1, Sabin poliovirus type 2 and Sabin poliovirus type 3.

6. The replication-competent recombinant poliovirus of claim 4 wherein the nucleic acid sequence of (a) encodes a polypeptide antigen selected from the group consisting of: bacterial polypeptide antigens, viral polypeptide antigens, fungal polypeptide antigens, and parasite polypeptide antigens.

7. The replication-competent recombinant poliovirus of claim 6 wherein the nucleic acid sequence of (a) encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

8. The replication-competent recombinant poliovirus of claim 2 wherein the exogenous nucleic acid sequence of (a) encodes a polypeptide antigen and the genome of the parent poliovirus is the genome of a Mahoney poliovirus.

9. The replication-competent recombinant poliovirus of claim 8 wherein the nucleic acid sequence of (a) encodes a polypeptide antigen selected from the group consisting of: bacterial polypeptide antigens, viral polypeptide antigens, fungal polypeptide antigens, and parasite polypeptide antigens.

10. A replication-competent recombinant poliovirus which expresses an exogenous polypeptide as a component of a recombinant polyprotein precursor that is proteolytically processed, with the result that the exogenous polypeptide is released from the recombinant polyprotein precursor, in which the recombinant genome comprises:
    a) an exogenous nucleic acid sequence encoding an exogenous polypeptide to be expressed;
    b) exogenous sequences which are polioviral proteolytic cleavage sites for the poliovirus 3C protease or for the poliovirus 2A protease; and
    c) the genome of a parent poliovirus,
wherein the exogenous nucleic acid sequence of (a) and nucleic acid sequences encoding artificial proteolytic cleavage sites for the poliovirus 3C protease or the poliovirus 2A protease of (b) are present in the recombinant poliovirus genome in the following order: 5' untranslated region of the poliovirus genome—poliovirus unique start codon—polio protein encoding region(s)—artificial 3C or 2A protease recognition site—exogenous nucleic acid sequence—artificial 3C or 2A protease recognition site—remainder of the poliovirus, and when expressed, the exogenous polypeptide is expressed as a component of the polyprotein precursor produced by the recombinant poliovirus, the polyprotein precursor is proteolytically processed by the recombinant poliovirus and the exogenous polypeptide is not included in a mature poliovirus particle produced by the replication-competent poliovirus.

11. The replication-competent recombinant poliovirus of claim 10 wherein the nucleic acid sequence of (a) encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

12. The replication-competent recombinant poliovirus of claim 10 wherein the exogenous nucleic acid sequence of (a) encodes a polypeptide antigen and the genome of the parent poliovirus is the genome of a Sabin poliovirus.

13. The replication-competent recombinant poliovirus of claim 12 wherein the Sabin poliovirus is selected from the group consisting of: Sabin poliovirus type 1, Sabin poliovirus type 2 and Sabin poliovirus type 3.

14. The replication-competent recombinant poliovirus of claim 12 wherein the nucleic acid sequence of (a) encodes a polypeptide antigen selected from the group consisting of: bacterial polypeptide antigens, viral polypeptide antigens, fungal polypeptide antigens, and parasite polypeptide antigens.

15. The replication-competent recombinant poliovirus of claim 14 wherein the nucleic acid sequence of (a) encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

16. The replication-competent recombinant poliovirus of claim 10 wherein the exogenous nucleic acid sequence of (a) encodes a polypeptide antigen and the genome of the parent poliovirus is the genome of a Mahoney poliovirus.

17. The replication-competent recombinant poliovirus of claim 16 wherein the nucleic acid sequence of (a) encodes a polypeptide antigen selected from the group consisting of: bacterial polypeptide antigens, viral polypeptide antigens, fungal polypeptide antigens, and parasite polypeptide antigens.

18. A method of producing a replication-competent recombinant poliovirus, which expresses an exogenous polypeptide as a component of a recombinant polyprotein precursor that is proteolytically processed with the result that the exogenous polypeptide is released from the recombinant polyprotein precursor, comprising the steps of:
   a) providing a poliovirus which in its natural life cycle produces a polyprotein precursor which is proteolytically processed;
   b) introducing into the genome of the poliovirus of (a)
      (1) an exogenous nucleic acid sequence encoding a polypeptide to be expressed; and
      (2) an exogenous sequence which is a polioviral proteolytic cleavage site and which is cleaved by a poliovirus protease, wherein the protease proteolytically processes a protein precursor produced by the poliovirus provided in (a),
wherein (b)(1) and (b)(2) are inserted into the genome of the poliovirus of (a) at a location such that they do not disrupt a viral sequence necessary for viral replication and when expressed, the exogenous polypeptide is expressed as a component of the polyprotein precursor produced by the recombinant poliovirus, the polyprotein precursor is proteolytically processed by the recombinant poliovirus and the exogenous polypeptide is not included in a mature poliovirus particle produced by the replication-competent poliovirus.

19. The method of claim 18 wherein the nucleic acid sequence of (b) (1) encodes a polypeptide antigen selected from the group consisting of: hepatitis B S antigen, hepatitis B pre-S 1 antigen, hepatitis B pre-S2 antigen, *B. pertussis* 69 kD outer membrane protein, Herpes simplex glycoprotein D, and rotavirus VP7 antigen, and combinations thereof.

20. A method of producing a replication-competent recombinant poliovirus which expresses an exogenous polypeptide as a component of a recombinant polyprotein precursor that is proteolytically processed with the result that the exogenous polypeptide is released from the polyprotein precursor, the method comprising the steps of:
   a) providing a parent poliovirus;
   b) introducing into the genome of the parent poliovirus of
      (a)(1) an exogenous nucleic acid sequence encoding a polypeptide to be expressed; and
      (2) a nucleic acid sequence encoding an artificial proteolytic cleavage site for a protease which proteolytically processes a polyprotein precursor produced by the parent poliovirus provided in (a),
wherein the exogenous nucleic acid sequence of (b)(1) and a nucleic acid sequence encoding an artificial proteolytic cleavage site of (b)(2) which is the poliovirus 3C protease or the poliovirus 2A protease are present in the recombinant poliovirus genome in the following order: 5' untranslated region of the parent poliovirus genome—unique poliovirus start codon—exogenous nucleic acid sequence of (b)(1)—nucleic acid sequence encoding the artificial proteolytic cleavage site of (b)(2)—second codon of the parent poliovirus genome—remainder of the parent poliovirus genome, and when expressed, the exogenous polypeptide is expressed as a component of the polyprotein precursor produced by the recombinant poliovirus, the polyprotein precursor is proteolytically processed by the recombinant poliovirus and the exogenous polypeptide is not included in a mature poliovirus particle produced by the replication-completion poliovirus.

21. The method of claim 20 wherein the nucleic acid sequence of (b)(1) encodes a polypeptide antigen selected from the group consisting of: hepatitis B S antigen, hepatitis B per-S1 antigen, hepatitis B pre-S2 antigen, *B. pertussis* 69 kD outer membrane protein, Herpes simplex glycoprotein D, and rotavirus VP7 antigen, and combinations thereof.

22. A method of producing a replication-competent recombinant poliovirus which expresses an exogenous polypeptide as a component of a recombinant polyprotein precursor that is proteolytically processed with the result that the exogenous polypeptide is released from the polyprotein precursor, the method comprising the steps of:
   a) providing a parent poliovirus;
   b) introducing into the genome of the parent poliovirus of
      (a)
      (1) an exogenous nucleic acid sequence encoding a polypeptide to be expressed; and
      (2) exogenous sequences which are polioviral proteolytic cleavage sites and which are cleaved by a poliovirus protease, wherein the protease proteolytically processes a polyprotein precursor produced by the parent poliovirus in (a),
wherein the unit of the exogenous nucleic acid sequence of (b)(1) and nucleic acid sequences encoding artificial proteolytic cleavage sites of (b)(2) is located at a site within the poliovirus genome selected from the group consisting of: 1) the junction between Vp1 and 2A; 2) the junction between 2A and 2B; and 3) the junction between 2C and 3A, and when expressed, the exogenous polypeptide is expressed as a component of the polyprotein precursor produced by the recombinant poliovirus, the polyprotein precursor is proteolytically processed by the recombinant poliovirus and the exogenous polypeptide is not included in a mature poliovirus particle produced by the replication-competent poliovirus.

23. The method of claim 22 wherein the nucleic acid sequence of (b)(1) encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

24. The method of claim 22 wherein the nucleic acid sequence of (b)(2) which encodes an artificial proteolytic cleavage site encodes the proteolytic cleavage site for the poliovirus 3C protease or the proteolytic cleavage site for the poliovirus 2A protease.

25. A method of immunizing an individual against a pathogen, comprising administering to the individual a replication-competent recombinant poliovirus of claim 1 wherein the exogenous nucleic acid sequence of (a) encodes an antigen of the pathogen, in sufficient quantity to produce an immune response in the individual.

26. A method of immunizing an individual against a pathogen, comprising administering to the individual a replication-competent recombinant poliovirus of claim 2 wherein the exogenous nucleic acid sequence of (a) encodes an antigen of the pathogen, in sufficient quantity to produce an immune response in the individual.

27. The method of claim 26 wherein the nucleic acid sequence of (a) encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

28. A method of immunizing an individual against a pathogen, comprising administering to the individual a replication-competent recombinant poliovirus of claim 6 wherein the exogenous nucleic acid sequence of (a) encodes an antigen of the pathogen, in sufficient quantity to produce an immune response in the individual.

29. (Twice amended) The method of claim 28 wherein the nucleic acid sequence of (a) encodes a polypeptide antigen selected from the group consisting of: hepatitis B S antigen, hepatitis B per-S1 antigen, hepatitis B pre-S2 antigen, *B. pertussis* 69 kD outer membrane protein, Herpes simplex glycoprotein D, and rotavirus VP7 antigen, and combinations thereof.

30. A method of producing a protein, comprising the steps of:
   a) introducing the replication-competent recombination poliovirus of claim 1 into an appropriate host cell; and
   b) maintaining the product of (a) under conditions appropriate for replication of the replication-competent poliovirus of claim 1.

31. The method of claim 30 wherein the host cell is a human cell.

32. A method of producing a protein, comprising the steps of:
   a) introducing the replication-competent recombinant poliovirus of claim 2 into an appropriate host cell; and
   b) maintaining the product of (a) under conditions appropriate for replication of the replication-competent poliovirus of claim 2.

33. The method of claim 32 wherein the nucleic acid sequence encoding an exogenous polypeptide to be expressed encodes a polypeptide antigen selected from the group consisting of: hepatitis B S antigen, hepatitis B per-S1 antigen, hepatitis B pre-S2 antigen, *B. pertussis* 69 kD outer membrane protein, Herpes simplex glycoprotein D, and rotavirus VP7 antigen, and combinations thereof.

34. A vaccine composition comprising a replication-competent recombinant poliovirus of claim 1 and a physiologically acceptable carrier.

35. A vaccine composition of claim 34 wherein the exogenous polypeptide of (a) is an antigen of a pathogen selected from the group consisting of: bacteria, fungi, viruses and parasites.

36. A vaccine composition comprising a replication-competent recombinant poliovirus of claim 2 and a physiologically acceptable carrier.

37. The vaccine composition of claim 36 wherein the nucleic acid sequence encoding an exogenous poly-peptide to be expressed encodes a polypeptide antigen selected from the group consisting of: bacterial polypeptide, antigens, viral polypeptide antigens, fungal polypeptide antigens and parasite polypeptide antigens.

38. The vaccine composition of claim 37 wherein the nucleic acid sequence encoding an exogenous polypeptide to be expressed encodes a polypeptide antigen selected from the group consisting of: hepatitis B S antigen, hepatitis B pre-S1 antigen, hepatitis B pre-S2 antigen, *B. pertussis* 69 kD outer membrane protein, Herpes simplex glycoprotein D, and rotavirus VP7 antigen, and combinations thereof.

39. A vaccine composition comprising a replication-competent recombinant poliovirus of claim 8 and a physiologically acceptable carrier.

40. The vaccine composition of claim 39 wherein the nucleic acid sequence encoding an exogenous polypeptide to be expressed encodes a polypeptide antigen selected from the group consisting of: bacterial polypeptide, antigens, viral polypeptide antigens, fungal polypeptide antigens and parasite polypeptide antigens.

41. A replication-competent recombinant poliovirus in which the recombinant genome includes an exogenous nucleic acid sequence encoding an exogenous polypeptide to be expressed and one or more exogenous sequences which is a poliovirus proteolytic cleavage site and which expresses the encoded polypeptide and induces production of antibodies specific for the exogenous polypeptide in a mammal into which they are introduced.

\* \* \* \* \*

UNITED STATES PATENT AND TRADEMARK OFFICE
CERTIFICATE OF CORRECTION

PATENT NO. : 5,965,124
DATED : October 12, 1999
INVENTOR(S) : Mark Feinberg, Raul Andino, Carolyn Louise Weeks-Levy and Patricia Anne Reilly It is certified that error appears in the above-identified patent and that said Letters Patent is hereby corrected as shown below:

In Claims:

In line 4 of Claims 21, 29 and 33 delete "per" and insert ---pre---.
In line 3 of Claim 30 delete "recombination" and insert ---recombinant---.
In line 2 of Claim 37, delete "poly-peptide" and insert ---polypeptide---.

Signed and Sealed this

Twenty-third Day of May, 2000

Attest:

Q. TODD DICKINSON

*Attesting Officer*  *Director of Patents and Trademarks*

```
                         SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TACGGTCGAC CTAATTACGA CTCACTATAG G                                  31

(2) INFORMATION FOR SEQ ID NO:2:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TTGAAACAAA GCCTCCCTCG AGGGGAATTC CTGAGCACCC ATTATG                  46

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCCTCGAGGG AGGCTTTGTT TCAAGGTGCT CAGGTTTCA                          39

(2) INFORMATION FOR SEQ ID NO:4:
```

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATTATCTGGT GCGGGAACAC AAAGGC                                              26

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TCAGGAATTC ACACCTCAAA ATATT                                               25

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCAGCTCGAG GGATTTGCCA TACTAAT                                             27

(2) INFORMATION FOR SEQ ID NO:7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CAGGATTTCA GTGTCACAAT GGAGAACATC ACATCAGGAT TTCTAGGACC                    50

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AACCCATATG TAACGAAACA AAGTTCCTCG AGTTCAT                                  37

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATCTTCGACG CGTTGCGCTC                                                   20

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

GTCCTAAAGT CACAGTGT                                                     18

(2) INFORMATION FOR SEQ ID NO:11:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GCTTTGTTTC AAGGAGCTCA AGTATCATCC CAA                                    33

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

TAATGGTGAT GGATCCTTCT                                                   20

(2) INFORMATION FOR SEQ ID NO:13:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GACAGGATTT CAGTGTCACA ATGGGGCAGA ATCTTTCCAC CAGCAAT                     47

(2) INFORMATION FOR SEQ ID NO:14:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

CTCTTTGTGA GTAGGAGTCC GGTACGTCAC CTTAAGGTGT T          41

(2) INFORMATION FOR SEQ ID NO:15:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GACAGGATTT CAGTGTCACA ATGCAGTGGA ATTCCACAAC CTTCCACCA          49

(2) INFORMATION FOR SEQ ID NO:16:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CTAAAGTCAC AGTGTTACCC GCCGGCGCAA TTGAATTAAT TCCGCGAAGG TGTC          54

(2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ATGGGCGGCC GCGTTAACTT AATTAAGGCG CTTCCACAGG GAGCTCAAGT ATCATCC          57

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TCACCTTCGT GGTAACCGCC AACT          24

(2) INFORMATION FOR SEQ ID NO:19:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TTCCAAACTG GTGTATACCG CCGGCGCAAT TGAATTAATT CCGCGAAGGT GTC          53

(2) INFORMATION FOR SEQ ID NO:20:

(i) SEQUENCE CHARACTERISTICS:
    (A) LENGTH: 58 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:20:

TATGGCGGCC GCGTTAACTT AATTAAGGCG CTTCCACAGG GCTTGGGCAT CAGAATAA        58

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GTCGTACCAC TGGTCGTGCT A                                                21

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CAGGATTTCA GTGTCACAAT GTACGGAATA GAATATACC                             39

(2) INFORMATION FOR SEQ ID NO:23:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GTCGCAAGAT AATGTCTCAT CGAAACAAAG TTCCTCG                               37

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (genomic)

(ix) FEATURE:
        (A) NAME/KEY: CDS
        (B) LOCATION: 5..22

(xi) SEQUENCE DESCRIPTION: SEQ ID NO:24:

CAUA AUG GGU GCU CAG GAA UUC                                           22
     Met Gly Ala Gln Glu Phe
      1               5

(2) INFORMATION FOR SEQ ID NO:25:

```
         (i) SEQUENCE CHARACTERISTICS:
              (A) LENGTH: 6 amino acids
              (B) TYPE: amino acid
              (D) TOPOLOGY: linear (ii) MOLECULE TYPE: protein (xi) SEQUENCE DESCRIPTION: SEQ ID NO:25:

Met Gly Ala Gln Glu Phe
 1               5

(2) INFORMATION FOR SEQ ID NO:26:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: RNA (genomic)

(ix) FEATURE:
              (A) NAME/KEY: CDS
              (B) LOCATION: 1..33

(xi) SEQUENCE DESCRIPTION: SEQ ID NO:26:

CCC UCG AGG GAG GCU UUG UUU CAA GGU GCU CAG                    33
Pro Ser Arg Glu Ala Leu Phe Gln Gly Ala Gln
 1               5                  10

(2) INFORMATION FOR SEQ ID NO:27:

(i) SEQUENCE CHARACTERISTICS:
              (A) LENGTH: 11 amino acids
              (B) TYPE: amino acid
              (D) TOPOLOGY: linear (ii) MOLECULE TYPE: protein (xi) SEQUENCE DESCRIPTION: SEQ ID NO:27:

Pro Ser Arg Glu Ala Leu Phe Gln Gly Ala Gln
 1               5                  10

(2) INFORMATION FOR SEQ ID NO:28:

(i) SEQUENCE CHARACTERISTICS:
              (A) LENGTH: 93 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: CDS
              (B) LOCATION: 1..93

(xi) SEQUENCE DESCRIPTION: SEQ ID NO:28:

ATG GGT GCT CAG GAA TTC GGA GCG GCC GCT GGA GCG CGC CTC GAG GGT    48
Met Gly Ala Gln Glu Phe Gly Ala Ala Ala Gly Ala Arg Leu Glu Gly
 1               5                  10                  15

GGC GGA GGT GGA GGC GAG GCT TTG TTT CAA GGT GCT CAG GTT TCA        93
Gly Gly Gly Gly Gly Glu Ala Leu Phe Gln Gly Ala Gln Val Ser
                 20                  25                  30

(2) INFORMATION FOR SEQ ID NO:29:

(i) SEQUENCE CHARACTERISTICS:
              (A) LENGTH: 31 amino acids
              (B) TYPE: amino acid
```

```
           (D) TOPOLOGY: linear (ii) MOLECULE TYPE: protein (xi) SEQUENCE DESCRIPTION: SEQ ID NO:29:

Met Gly Ala Gln Glu Phe Gly Ala Ala Ala Gly Ala Arg Leu Glu Gly
 1               5                  10                  15

Gly Gly Gly Gly Gly Glu Ala Leu Phe Gln Gly Ala Gln Val Ser
                20                  25                  30

(2) INFORMATION FOR SEQ ID NO:30:

(i) SEQUENCE CHARACTERISTICS:
           (A) LENGTH: 99 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: CDS
           (B) LOCATION: 1..99

(xi) SEQUENCE DESCRIPTION: SEQ ID NO:30:

CTG ACC ACA TAT GGA TTC GGA CAC GGC GGA GGT GGG GGA GGT GAA TTC        48
Leu Thr Thr Tyr Gly Phe Gly His Gly Gly Gly Gly Gly Gly Glu Phe
 1               5                  10                  15

GGA GCG GCC GCT GGA GCG CGC GGT CTC GAG GAT CTG ACC ACA TAT GGA        96
Gly Ala Ala Ala Gly Ala Arg Gly Leu Glu Asp Leu Thr Thr Tyr Gly
                20                  25                  30

TTC                                                                    99
Phe (2) INFORMATION FOR SEQ ID NO:31:

(i) SEQUENCE CHARACTERISTICS:
           (A) LENGTH: 33 amino acids
           (B) TYPE: amino acid
           (D) TOPOLOGY: linear (ii) MOLECULE TYPE: protein (xi) SEQUENCE DESCRIPTION: SEQ ID NO:31:

Leu Thr Thr Tyr Gly Phe Gly His Gly Gly Gly Gly Gly Gly Glu Phe
 1               5                  10                  15

Gly Ala Ala Ala Gly Ala Arg Gly Leu Glu Asp Leu Thr Thr Tyr Gly
                20                  25                  30

Phe (2) INFORMATION FOR SEQ ID NO:32:

(i) SEQUENCE CHARACTERISTICS:
           (A) LENGTH: 111 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: CDS
           (B) LOCATION: 1..111

(xi) SEQUENCE DESCRIPTION: SEQ ID NO:32:

CTG ACC ACA TAT GGA TTC GGA CAC GCC ATG GAA CAA GGC GGA GGT GGG        48
Leu Thr Thr Tyr Gly Phe Gly His Ala Met Glu Gln Gly Gly Gly Gly
 1               5                  10                  15
```

```
CGA GGT CAA TTC GGA GCG GCC GCT GCA GCC CGC GGT CTC GAG CAT CTG      96
Arg Gly Gln Phe Gly Ala Ala Ala Ala Ala Arg Gly Leu Glu His Leu
            20                  25                  30

ACC ACA TAT GGA TTC                                                 111
Thr Thr Tyr Gly Phe
        35
```

(2) INFORMATION FOR SEQ ID NO:33:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:33:

```
Leu Thr Thr Tyr Gly Phe Gly His Ala Met Glu Gln Gly Gly Gly
 1               5                  10                  15

Arg Gly Gln Phe Gly Ala Ala Ala Ala Ala Arg Gly Leu Glu His Leu
            20                  25                  30

Thr Thr Tyr Gly Phe
        35
```

(2) INFORMATION FOR SEQ ID NO:34:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..93

(xi) SEQUENCE DESCRIPTION: SEQ ID NO:34:

```
GAA GCC ATG GAA CAA GGA CCA CTC CAG TAT GAA TTC GGA GCG GCC GCT     48
Glu Ala Met Glu Gln Gly Pro Leu Gln Tyr Glu Phe Gly Ala Ala Ala
 1               5                  10                  15

GGA GCG CGC GGT CTC GAG GCT TTG TTT CAA GGC ATC ACC AAT TAC         93
Gly Ala Arg Gly Leu Glu Ala Leu Phe Gln Gly Ile Thr Asn Tyr
            20                  25                  30
```

(2) INFORMATION FOR SEQ ID NO:35:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:35:

```
Glu Ala Met Glu Gln Gly Pro Leu Gln Tyr Glu Phe Gly Ala Ala Ala
 1               5                  10                  15

Gly Ala Arg Gly Leu Glu Ala Leu Phe Gln Gly Ile Thr Asn Tyr
            20                  25                  30
```

(2) INFORMATION FOR SEQ ID NO:36:

(i) SEQUENCE CHARACTERISTICS:
        (A) LENGTH: 78 base pairs
        (B) TYPE: nucleic acid
        (C) STRANDEDNESS: single (D) TOPOLOGY: linear (ii) MOLECULE TYPE: DNA (genomic)

(ix) FEATURE:
        (A) NAME/KEY: CDS
        (B) LOCATION: 1..78

(xi) SEQUENCE DESCRIPTION: SEQ ID NO:36:

```
GAG GCT TTG TTT CAA GGC ATC ACC AAT GAA TTC AGC GGC CGC TCG AGG      48
Glu Ala Leu Phe Gln Gly Ile Thr Asn Glu Phe Ser Gly Arg Ser Arg
 1               5                  10                  15

GAG GCC ATG GAA CAA GGA CCA CTC CAG TAT                              78
Glu Ala Met Glu Gln Gly Pro Leu Gln Tyr
             20                  25
```

(2) INFORMATION FOR SEQ ID NO:37:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:37:

```
Glu Ala Leu Phe Gln Gly Ile Thr Asn Glu Phe Ser Gly Arg Ser Arg
 1               5                  10                  15

Glu Ala Met Glu Gln Gly Pro Leu Gln Tyr
             20                  25
```

(2) INFORMATION FOR SEQ ID NO:38:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..75

(xi) SEQUENCE DESCRIPTION: SEQ ID NO:38:

```
ACA GCA AAG GTA CAA GGC ATC ACC AAT GAA TTC AGC GGC CGC TCG AGG      48
Thr Ala Lys Val Gln Gly Ile Thr Asn Glu Phe Ser Gly Arg Ser Arg
 1               5                  10                  15

GAG GCC ATG GAA CAA GGA GGG TTC GAT                                  75
Glu Ala Met Glu Gln Gly Gly Phe Asp
             20                  25
```

(2) INFORMATION FOR SEQ ID NO:39:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:39:

```
Thr Ala Lys Val Gln Gly Ile Thr Asn Glu Phe Ser Gly Arg Ser Arg
 1               5                  10                  15

Glu Ala Met Glu Gln Gly Gly Phe Asp
             20                  25
```